US012708680B2

(12) United States Patent
Haaland et al.

(10) Patent No.: US 12,708,680 B2
(45) Date of Patent: Aug. 18, 2026

(54) SELECTIVE ACOUSTIC DISRUPTION OF PATHOGENS

(71) Applicant: NOPIOID, LLC, Fraser, CO (US)

(72) Inventors: Peter Donald Haaland, Rowley, MA (US); Howland Shaw Warren, Cambridge, MA (US)

(73) Assignee: NOPIOID, LLC, Fraser, CO (US)

(*) Notice: Subject to any disclaimer, the term of this patent is extended or adjusted under 35 U.S.C. 154(b) by 270 days.

(21) Appl. No.: 18/056,407

(22) Filed: Nov. 17, 2022

(65) Prior Publication Data

US 2023/0158182 A1 May 25, 2023

Related U.S. Application Data

(60) Provisional application No. 63/280,720, filed on Nov. 18, 2021.

(51) Int. Cl.
*A61L 2/025* (2006.01)
*A61L 2/26* (2006.01)

(52) U.S. Cl.
CPC ................ *A61L 2/025* (2013.01); *A61L 2/26* (2013.01)

(58) Field of Classification Search
CPC .. A61L 2/025; A61L 2/26; A61N 7/02; A61N 2007/0039; A61N 2007/0078
See application file for complete search history.

(56) References Cited

U.S. PATENT DOCUMENTS

| | | | | | |
|---|---|---|---|---|---|
| 5,558,092 | A * | 9/1996 | Unger | A61B 8/0833 | 601/3 |
| 5,656,016 | A * | 8/1997 | Ogden | A61M 37/0092 | 604/290 |
| 6,450,979 | B1 * | 9/2002 | Miwa | A61H 23/0245 | 601/2 |
| 8,303,898 | B2 * | 11/2012 | Ronholdt | A61L 2/28 | 422/1 |
| 8,679,103 | B2 * | 3/2014 | Krespi | A61B 18/26 | 606/2 |
| 2003/0032900 | A1 * | 2/2003 | Ella | A61N 5/0616 | 601/123 |
| 2005/0137656 | A1 * | 6/2005 | Malak | A61N 5/0616 | 607/88 |
| 2005/0196725 | A1 * | 9/2005 | Fu | A61C 17/0211 | 433/216 |
| 2008/0305467 | A1 * | 12/2008 | Ussing | G01V 1/133 | 435/173.7 |

(Continued)

FOREIGN PATENT DOCUMENTS

| | | | | |
|---|---|---|---|---|
| CA | 2317777 C | * 5/2005 | A61M 37/0092 |
| EP | 1060728 A1 | * 12/2000 | A61H 23/0245 |

(Continued)

OTHER PUBLICATIONS

International Search Report and Written Opinion for Application No. PCT/US2022/080023 dated Apr. 7, 2023 (19 pages).

(Continued)

*Primary Examiner* — Regina M Yoo
(74) *Attorney, Agent, or Firm* — Michael Best & Friedrich LLP

(57) ABSTRACT

Described herein are methods and devices for selectively diminishing viability of or killing bacterial, fungal, or viral pathogens using acoustic excitation below the thresholds for cavitation.

25 Claims, 28 Drawing Sheets

(56) References Cited

U.S. PATENT DOCUMENTS

2011/0213281 A1* 9/2011 Iger .......................... A61N 7/00 601/2
2015/0283277 A1* 10/2015 Schafer ................. A61L 2/0029 422/128
2015/0314021 A1* 11/2015 Botos ...................... A61L 2/183 422/128
2016/0015478 A1 1/2016 Jolesz et al.
2016/0310766 A1* 10/2016 Cioanta .................... A61N 7/00
2019/0175954 A1* 6/2019 Levy .................... A61B 8/4494
2019/0225521 A1 7/2019 Heath
2019/0328354 A1 10/2019 Xu et al.
2020/0164194 A1 5/2020 Leighton et al.
2022/0266046 A1* 8/2022 Giles ..................... A61F 7/0053
2022/0331611 A1* 10/2022 Razavi ................. C12N 5/0676

FOREIGN PATENT DOCUMENTS

GB 2303552 A * 2/1997 ............... A61N 7/00
JP H03123559 A * 5/1991
WO WO-2014153257 A2 * 9/2014 ............... A61N 1/44
WO 2018132443 A1 7/2018

OTHER PUBLICATIONS

Zhou, B. "Investigation on factors influencing ultrasound assisted surface decontamination of fresh and fresh-cut vegetables." Dissertation. University of Illinois at Urbana-Champaign (2010): pages ii, iii, 20, 21, 23, 26, 51, 80, 122, 125, 134 & 153.
Hu, H., et al. "Stretchable ultrasonic transducer arrays for three-dimensional imaging on complex surfaces." Science advances 4.3 (2018): eaar3979.
Lee, J., et al. "Development of dual-frequency oblong-shaped-focused transducers for intravascular ultrasound tissue harmonic imaging." IEEE Transactions on Ultrasonics, Ferroelectrics, and Frequency Control 65.9 (2018): 1571-1582.
Muldur, S., et al. "Measuring spontaneous neutrophil motility signatures from a drop of blood using microfluidics." Methods in cell biology. vol. 147. Academic Press, 2018. 93-107.

* cited by examiner

FIG. 1

251
252
253
254
255
freq(1)=5E5 Hz Surface: Total acoustic pressure field (Pa)
z coordinate (mm)
r coordinate (mm)
256
257
8.04×10^5
-8.61×10^5
×10^5

1.Cephalic vein
2.Biceps (long head)
3.Biceps (short head)
4.Brachialis
5.Musculocutaneous nerve
6.Brachial artery and vein
7.Median nerve
8.Humeral shaft
9.Radial nerve
10.Profunda Brachii artery and vein
11.Triceps (medial head)
12.Ulnar nerve
13.Triceps (lateral head)
14.Triceps (long head)

FIG. 7B 702
703
704
701

SELECTIVE ACOUSTIC DISRUPTION OF PATHOGENS

CROSS-REFERENCE TO RELATED APPLICATIONS

This application claims priority to U.S. Provisional Application No. 63/280,720, filed Nov. 18, 2021, which is incorporated by reference herein in its entirety.

TECHNICAL FIELD

Described herein are methods and devices for selectively compromising the integrity of membranes in bacterial, fungal, or viral pathogens using tailored acoustic excitation below the thresholds for cavitation.

BACKGROUND

Acoustic radiation has been routinely applied to non-invasive imaging of biological tissues at low intensities and to gross mechanical disruption of macroscopic targets such as kidney stones or tumors at substantially higher intensities.

Pathogens evolve in the changing environment of passive humoral and active medical interventions, where they gradually develop resistance to established antibacterial, antiviral, and antifungal medications. These antibiotic resistant organisms cause substantial pain, suffering, expense, and death. New pharmaceutical interventions are being developed, but these represent variations in chemistry—different in degree from prior art, but not in kind. A qualitatively different approach to pathogen control based on mechanisms different than administration of chemicals is urgently needed to replace or complement pharmaceutical therapies.

Pathogens such as bacteria and fungi maintain their architecture through internal pressure against a cell wall or membrane. Bacteria have peptidoglycan compositions within their cell envelopes and maintain cellular turgor using osmotic pressures. Fungi have cell walls primarily formed with rigid polysaccharides outside of a protein-based plasma membrane and stabilized by the lipid ergosterol. Fungi also generate internal hydrostatic pressures by osmotic control. Virus particles have capsids formed from peptides that are augmented by lipid capsules in some species. Viral pathogens generate internal pressure of as much as 100 atmospheres from compressive molecular strain due to the incommensurate dimensions of nucleic acid chain length and virus diameter, and from electrostatic repulsion among charged moieties.

Contrasting with pathogens, somatic cells maintain their shape primarily through internal filamentous proteins such as actin and integrin. Somatic membranes are comprised of lipid bilayers approximately 5 nm thick and play a minor role as a stress-bearing component of a cell. Moreover, somatic cells have internal pressures within a few percent of ambient (101 kPa); the primary role of the membrane is to convey nutrients into and waste out of the cellular envelope.

Metaphorically, somatic cells are like a mountaineering tent with a thin shell whose shape is set by internal poles and cords that are in tension and compression. Pathogens are more like swollen basketballs with internal pressures as much as one hundred times ambient. This qualitative difference in mechanical properties between normal cells and pathogens provides a basis for selective mechanical disruption of pathogens using acoustic pressure and high-cycle fatigue.

What is needed are methods for selectively disrupting pathogen cells using acoustic radiation.

SUMMARY

One embodiment described herein is a method for selectively diminishing viability of or killing a pathogen in a surrounding medium containing somatic cells by administering greater than ten thousand cycles of pressure variation below the threshold for cavitation of the surrounding medium. In one aspect, the pathogen is a cell having an internal static pressure of greater than 20 kPa above that of the surrounding medium. In another aspect, the pathogen is a bacterium. In another aspect, the pathogen is a fungus. In another aspect, the pathogen is a virus. In another aspect, the administration is by an acoustic transducer where the shape, frequency, amplitude, and orientation of the acoustic transducer is selected by finite element acoustic analysis of the surrounding medium and of the pathogen. In another aspect, the acoustic analysis permits application of pressure cycles at specific sites without causing excessive frictional heating or cavitation. In another aspect, the acoustic transducer is external to a human body of a subject. In another aspect, the acoustic transducer penetrates the human body of the subject to make acoustic contact with a targeted tissue or an internal structure. In another aspect, the acoustic transducer is shaped and excited to irradiate an extracorporeal fluid with greater than ten thousand cycles of pressure variation, wherein the amplitude, frequency, and number of the cycles of pressure variation diminish pathogen viability without causing cavitation or excessive heating of the surrounding medium. In another aspect, the cycles of pressure variation are selected to enable, accelerate, or potentiate the action of an antimicrobial pharmaceutical agent. In another aspect, the surrounding medium geometry and composition are determined by biomedical imaging. In another aspect, the biomedical imaging is tomographic. In another aspect, the acoustic transducer is a conformable piezoelectric transducer array, comprising: a silicone elastomer substrate and a silicone elastomer superstrate; a plurality of piezoelectric transducer elements disposed between the substrates and superstrate; a first electrical interconnect layer electrically interconnecting a first surface of the plurality of piezoelectric transducer elements adjacent to the silicone elastomer substrate; and a second electrical interconnect layer electrically interconnecting a second surface of the plurality of piezoelectric transducer elements adjacent to the silicone elastomer superstrate. In another aspect, at least one of the plurality of piezoelectric transducer elements comprises a 1-3 composite material. In another aspect, each of the plurality of piezoelectric transducer elements comprises a 1-3 composite material. In another aspect, the first and second electrical interconnect layers have a patterned island and bridge structure that includes a plurality of islands electrically interconnected by bridges, each of the plurality of piezoelectric transducer elements being supported by one of the islands.

Another embodiment described herein is a method for treating a subject infected by one or more pathogens using an acoustic transducer to selectively diminish the viability of or kill the one or more pathogens, the method comprising: contacting the acoustic transducer to an external surface of the subject's body such that the acoustic transducer conforms to a shape of the external surface, the acoustic transducer being a conformable piezoelectric transducer array, comprising: a silicone elastomer substrate and a silicone elastomer superstrate; a plurality of piezoelectric transducer elements disposed between the substrates and superstrate; a first electrical interconnect layer electrically interconnecting a first surface of the plurality of piezoelectric transducer elements adjacent to the silicone elastomer substrate; and a second electrical interconnect layer electrically interconnecting a second surface of the plurality of piezoelectric transducer elements adjacent to the silicone elastomer superstrate; and administering greater than ten thousand cycles of pressure variation into the subject using the acoustic transducer to penetrate the surface of the subject's body and make acoustic contact with the one or more pathogens. In one aspect, the method further comprises, optionally imaging the subject's body prior to and/or following the administering greater than ten thousand cycles of pressure variation, where the imaging comprises: transmitting ultrasound waves into the subject's body using the piezoelectric transducer array; receiving ultrasound waves from the subject body using the piezoelectric transducer array; and displaying an indication of the received ultrasound waves. In another aspect, the one or more pathogens is a cell having an internal static pressure of greater than 20 kPa above that of a surrounding medium. In another aspect, the one or more pathogens is a bacterium, fungus, virus, or combinations thereof. In another aspect, the cycles of pressure variation are below the threshold for cavitation or excessive heating of the surrounding medium. In another aspect, at least one of the plurality of piezoelectric transducer elements comprises a 1-3 composite material. In another aspect, each of the plurality of piezoelectric transducer elements comprises a 1-3 composite material. In another aspect, the first and second electrical interconnect layers have a patterned island and bridge structure that includes a plurality of islands electrically interconnected by bridges, each of the plurality of piezoelectric transducer elements being supported by one of the islands.

Another embodiment described herein is an acoustic transducer in mechanical contact with a living organism, the acoustic transducer configured to generate high cycle acoustic pressures for selectively diminishing the viability of or killing a pathogen without disrupting the living organism's somatic cells. In one aspect, the acoustic transducer is affixed to a surface of the living organism with an adhesive cement. In another aspect, the acoustic transducer penetrates a tissue of the living organism and makes acoustic contact with an internal structure whose elastic modulus exceeds that of a surrounding tissue. In another aspect, the internal structure is a bone. In another aspect, the internal structure is an implanted inorganic material. In another aspect, the internal structure is a metallic, ceramic, biomimetic composite, or biocompatible material. In another aspect, the acoustic transducer contacts a surface of a wart or lesion on the living organism generated by a viral, bacterial, or fungal infection. In another aspect, the acoustic transducer directs transient external pressures to an abscess on the living organism. In another aspect, the acoustic transducer directs transient external pressures to one or more teeth of the living organism for diminishing the viability or killing of adsorbed bacteria or fungi. In another aspect, the high cycle acoustic pressures comprise greater than ten thousand cycles of pressure variation. In another aspect, the acoustic transducer is a conformable piezoelectric transducer array, comprising: a silicone elastomer substrate and a silicone elastomer superstrate; a plurality of piezoelectric transducer elements disposed between the substrates and superstrate; a first electrical interconnect layer electrically interconnecting a first surface of the plurality of piezoelectric transducer elements adjacent to the silicone elastomer substrate; and a second electrical interconnect layer electrically interconnecting a second surface of the plurality of piezoelectric transducer elements adjacent to the silicone elastomer superstrate. In another aspect, at least one of the plurality of piezoelectric transducer elements comprises a 1-3 composite material. In another aspect, each of the plurality of piezoelectric transducer elements comprises a 1-3 composite material. In another aspect, the first and second electrical interconnect layers have a patterned island and bridge structure that includes a plurality of islands electrically interconnected by bridges, each of the plurality of piezoelectric transducer elements being supported by one of the islands.

Another embodiment described herein is the use of any of the methods described herein or the transducers described herein for selectively diminishing viability of or killing a pathogen in a surrounding medium containing somatic cells by administering greater than ten thousand cycles of pressure variation below the threshold for cavitation of the surrounding medium in a subject in need thereof.

BRIEF DESCRIPTION OF THE DRAWINGS

FIG. 1 shows an illustration of a tensegrity network of stiff rods maintained in compression with filaments held in tension.

FIG. 3B plots the strain energy of the internal fluid, shell, and total of the model as a function of acoustic pressure. FIG. 3C plots the average strain for the membrane (306) and core as a function of acoustic pressure.

FIG. 7A-B show a model cross-section of a human limb (FIG. 7A) with bone (704) enveloped by muscle (703) and skin (702) and simplified with addition of a curved acoustic transducer (701) (FIG. 7B).

FIG. 15A shows a schematic illustrating the device structure. FIG. 15B shows an exploded view to illustrate each component in an element. FIG. 15C shows the optical image (bottom view) of four elements, showing the morphology of the piezoelectric material and bottom electrodes. FIG. 15D shows a tilted scanning electron microscopy image of a 1-3 piezoelectric composite. FIG. 15E shows the optical image (top view) of four elements, showing the morphology of the backing layer and top electrodes. FIG. 15F-H show optical images of this stretchable device when bent around a developable surface (FIG. 15F), wrapped on a nondevelopable surface (FIG. 15G), and in a mixed mode of folding, stretching, and twisting (FIG. 15H), showing its mechanical robustness. See U.S. Pat. App. Pub. No. US 2019/0328354 A1, which is incorporated by reference herein for such teachings.

DETAILED DESCRIPTION

Figure 2:
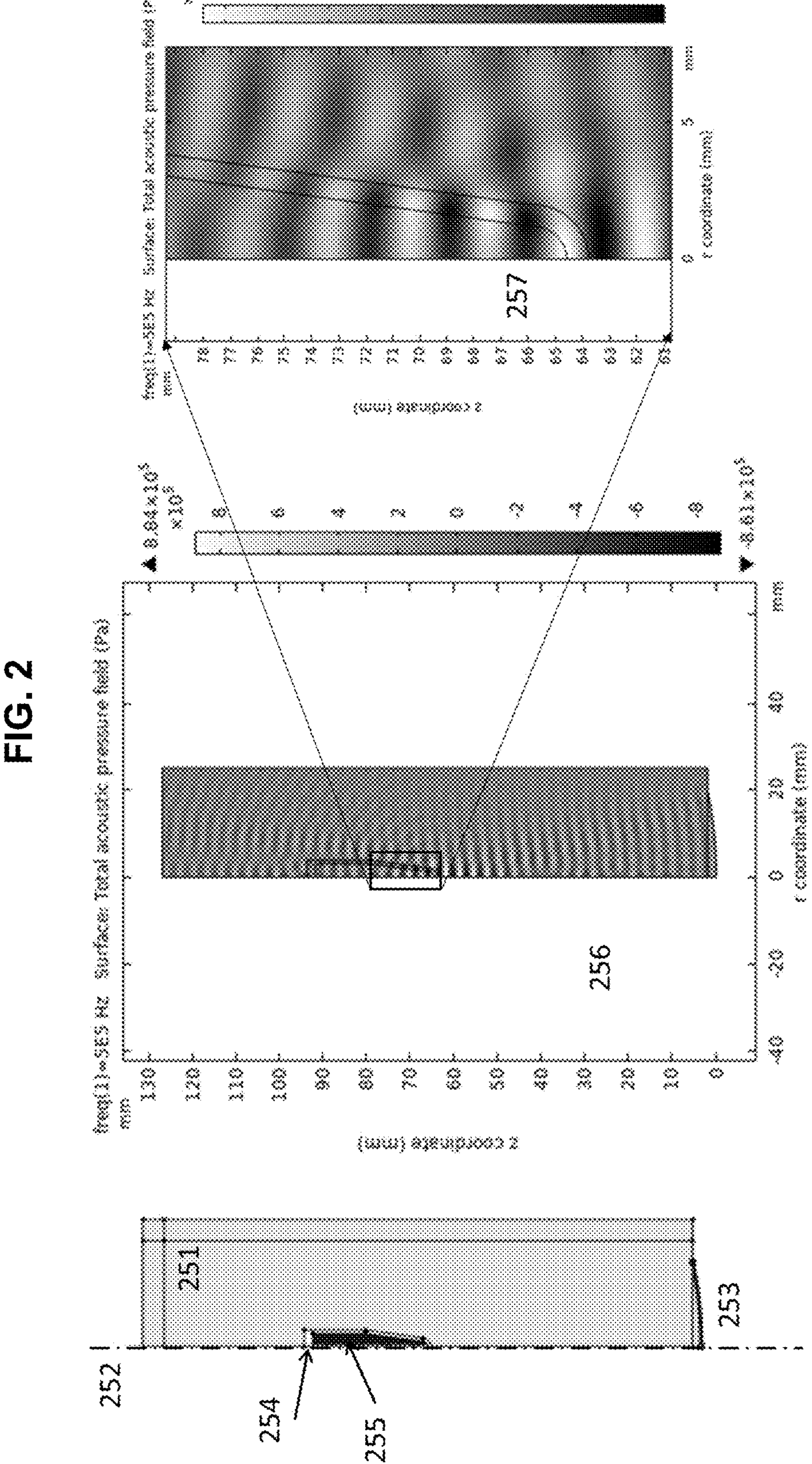
FIG. 2 shows geometry and calculated acoustic pressure profiles for excitation of a medium at 10 W/cm$^2$ and 500 kHz.

Unless otherwise defined, all technical and scientific terms used herein have the same meaning as commonly understood by one of ordinary skill in the art. For example, any nomenclatures used in connection with, and techniques of, cell and tissue culture, molecular biology, immunology, microbiology, genetics, and protein and nucleic acid chemistry and hybridization described herein are well known and commonly used in the art. In case of conflict, the present disclosure, including definitions, will control. Exemplary methods and materials are described below, although methods and materials similar or equivalent to those described herein can be used in practice or testing of the embodiments and aspects described herein.

As used herein, the terms such as "include," "including," "contain," "containing," "having," and the like mean "comprising." The present disclosure also contemplates other embodiments "comprising," "consisting of," and "consisting essentially of," the embodiments or elements presented herein, whether explicitly set forth or not.

As used herein, the term "a," "an," "the" and similar terms used in the context of the disclosure (especially in the context of the claims) are to be construed to cover both the singular and plural unless otherwise indicated herein or clearly contradicted by the context. In addition, "a," "an," or "the" means "one or more" unless otherwise specified.

As used herein, the term "or" can be conjunctive or disjunctive.

As used herein, the term "substantially" means to a great or significant extent, but not completely.

As used herein, the term "about" or "approximately" as applied to one or more values of interest, refers to a value that is similar to a stated reference value, or within an acceptable error range for the particular value as determined by one of ordinary skill in the art, which will depend in part on how the value is measured or determined, such as the limitations of the measurement system. In one aspect, the term "about" refers to any values, including both integers and fractional components that are within a variation of up to ±10% of the value modified by the term "about." Alternatively, "about" can mean within 3 or more standard deviations, per the practice in the art. Alternatively, such as with respect to biological systems or processes, the term "about" can mean within an order of magnitude, in some embodiments within 5-fold, and in some embodiments within 2-fold, of a value. As used herein, the symbol "~" means "about" or "approximately."

All ranges disclosed herein include both end points as discrete values as well as all integers and fractions specified within the range. For example, a range of 0.1-2.0 includes 0.1, 0.2, 0.3, 0.4 . . . 2.0. If the end points are modified by the term "about," the range specified is expanded by a variation of up to ±10% of any value within the range or within 3 or more standard deviations, including the end points.

The terms "first," "second," "third," and the like, as used herein, do not denote any order, quantity, or importance, but rather are used to distinguish one element from another.

As used herein, the terms "control," or "reference" are used herein interchangeably. A "reference" or "control" level may be a predetermined value or range, which is employed as a baseline or benchmark against which to assess a measured result. "Control" also refers to control experiments or control cells.

The term "substantially," as used herein, represents the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

As used herein, the term "subject" refers to an animal. Typically, the subject is a mammal. A subject also refers to primates (e.g., humans, male or female; infant, adolescent, or adult), non-human primates, rats, mice, rabbits, pigs, cows, sheep, goats, horses, dogs, cats, fish, birds, and the like. In one embodiment, the subject is a primate. In one embodiment, the subject is a human.

As used herein, a subject is "in need of treatment" if such subject would benefit biologically, medically, or in quality of life from such treatment. A subject in need of treatment does not necessarily present symptoms, particular in the case of preventative or prophylaxis treatments.

As used herein, the terms "inhibit," "inhibition," or "inhibiting" refer to the reduction or suppression of a given biological process, condition, symptom, disorder, or disease, or a significant decrease in the baseline activity of a biological activity or process.

As used herein, the terms "effective amount" or "therapeutically effective amount," refers to a substantially nontoxic, but sufficient amount of an action, agent, composition, or cell(s) being administered to a subject that will prevent, treat, or ameliorate to some extent one or more of the symptoms of the disease or condition being experienced or that the subject is susceptible to contracting. The result can be the reduction or alleviation of the signs, symptoms, or causes of a disease, or any other desired alteration of a biological system. An effective amount may be based on factors individual to each subject, including, but not limited to, the subject's age, size, type or extent of disease, stage of the disease, route of administration, the type or extent of supplemental therapy used, ongoing disease process, and type of treatment desired.

As used herein, "treatment" or "treating" refers to prophylaxis of, preventing, suppressing, repressing, reversing, alleviating, ameliorating, or inhibiting the progress of biological process including a disorder or disease, or completely eliminating a disease. A treatment may be either performed in an acute or chronic way. The term "treatment" also refers to reducing the severity of a disease or symptoms associated with such disease prior to affliction with the disease. "Repressing" or "ameliorating" a disease, disorder, or the symptoms thereof involves administering a cell, composition, or compound described herein to a subject after clinical appearance of such disease, disorder, or its symptoms. "Prophylaxis of" or "preventing" a disease, disorder, or the symptoms thereof involves administering a cell, composition, or compound described herein to a subject prior to onset of the disease, disorder, or the symptoms thereof. "Suppressing" a disease or disorder involves administering a cell, composition, or compound described herein to a subject after induction of the disease or disorder thereof but before its clinical appearance or symptoms thereof have manifest.

The term "pathogen," as used herein, refers to one or more of bacteria, fungi, or virus that disrupt the physiology of host organisms.

The term "biomimetic," as used herein, refers to compositions of matter that have thermal, mechanical, or acoustic properties that are matched within 5% to those of corresponding living tissues.

The term "biocompatible," as used herein refers to compositions that are chemically and biologically inert when introduced into living tissues.

Viral, bacterial, and fungal pathogens all comprise an interior region encapsulated by a membrane that separates them from the environment. In most known pathogens the interior contents are maintained at elevated pressures. Intracellular pressures over 5 megapascals (5 MPa) have been experimentally reported. Bacteria and fungi are pressurized by osmotic gradients that require metabolism to generate the necessary energy. The internal pressures of viruses, which have no metabolic activity, are generated by ATP driven compressive injection of the viral RNA or DNA into the viral capsid during replication, and electrostatic forces among charged nucleic acid residues. The mechanical compliance of the aqueous fluids inside and outside of enveloping membranes is substantially higher than that of the membranes themselves. The feature that distinguishes somatic cells from pathogens is that the pathogens' envelopes, whether in bacteria, fungi, or viruses, are pre-stressed by elevated internal hydrostatic pressures. At a cellular level, an abrupt change in the external acoustic pressure entails compressive, tensile, and shear stresses and strains that are concentrated in the pathogens' membranes. When these forces are applied at high frequency the process of high cycle fatigue disrupts the mechanical integrity of the membrane, selectively compromising the viability of the pathogen.

Design Factors

Figure 1:
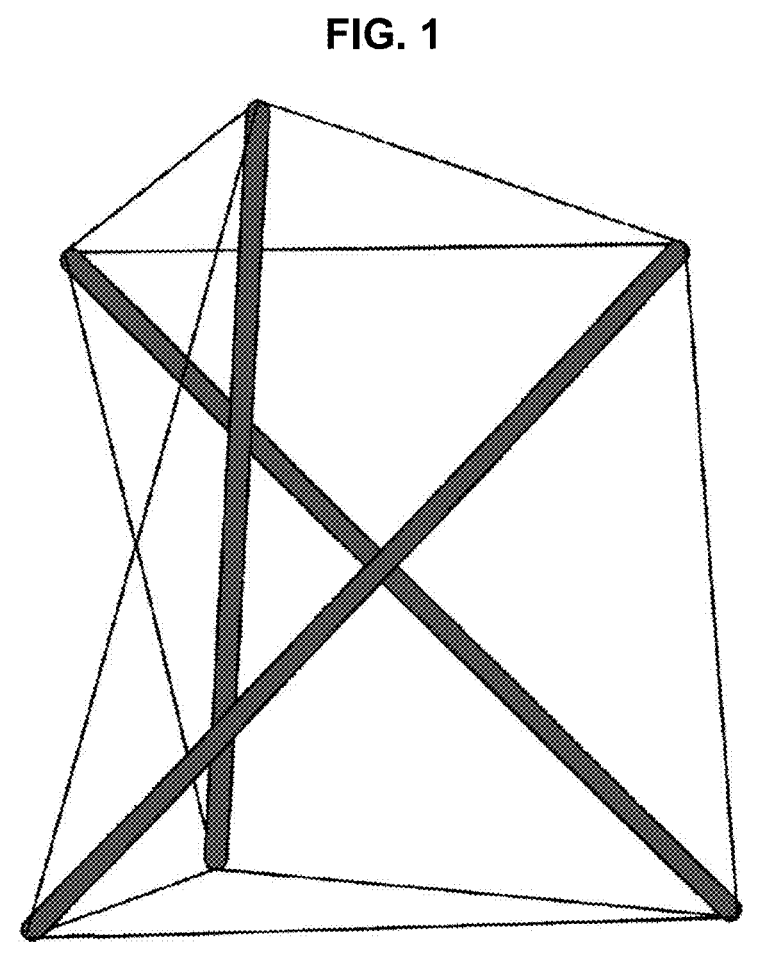

There is an essential and qualitative difference between most pathogens and mammalian somatic cells based on their mechanical structures. The architecture of somatic cells is bounded by a lipid membrane and maintained by a mechanical network of internal actin filaments, microtubules, or cytoskeleton. The cytoskeleton is a 'tensegrity' structure that responds to external forces by flexure, schematically shown in FIG. 1. Somatic cells have measured internal hydrostatic pressures of a few hundred to a few thousand Pascals. In other words, the internal pressure of somatic cells is less than 2% of the ambient pressure of 101 kPa (1 atmosphere).

Pathogens including bacteria, fungi, and viruses are also bounded by membranes but have tens to hundreds of kilopascals of internal pressure that pre-stresses their membranous envelopes. Bacteria and fungi are living cells that generate internal pressure using metabolic energy processes to drive osmotic pressure gradients. Viruses have no internal metabolism but generate internal pressure by molecular compression and electrostatic repulsions among charged nucleic acid residues. The energy for this process is provided by host-derived ATP during viral replication when the viral RNA or DNA is inserted into the viral capsid.

This feature, along with the observation that the cellular contents of pathogens are virtually incompressible fluids, implies that rapid changes in external pressure will generate stress and strain primarily in the membrane rather than the pathogen's internal constituents.

A normal mammalian somatic cell easily deforms over its entire volume in response to acoustic excitation, reducing the stress and strain on the membrane. Another way to describe this difference is that the Poisson ratio of the pathogen's internal constituents is close to zero and its bulk modulus is greater than $10^9$ Pa while its membrane has a bulk modulus of a few MPa and a Poisson ratio in the 0.3-0.5 range. Somatic cells, by contrast, flexibly deform in response to fluctuating acoustic perturbations because they are not pre-stressed by internal fluid pressures. Somatic cells go with the flow induced by transient pressure fluctuations.

The methods described herein seek to exploit high-cycle fatigue to selectively disrupt the integrity of pathogens' membranes while preserving the integrity of normal somatic cells. The method is illustrated with reference to FIG. 2 which displays a cross-section of an experiment to establish appropriate conditions for treating *Staphylococcus aureus* bacteria in aqueous media. A cylindrical vessel filled with degassed water (251) is defined by a cylindrical symmetry axis (252) and a piezoelectric membrane (253) that vibrates at 500 kHz with an amplitude of 35 nm. A small polypropylene tube (254) is filled with specimens (255) to be acoustically irradiated. Since the detailed physical properties of these materials is crucial to understanding the deposition of acoustic power in the specimens (255) we use finite element methods such as are available from Comsol (Comsol Multiphysics ver. 5.6, Burlington, Mass.) to define the acoustic pressure field surrounding the samples. This field is displayed in (256) and in a close-up view (257) in FIG. 2, where the peak acoustic pressure is ±800 kPa or approximately 8 atmospheres.

The methods described herein require precise understanding or estimation of the acoustic pressure field as it evolves from a transducer to the tissue being treated. The results in FIG. 2 show that the peak acoustic pressure between the transducer and sample, which are modulated by the laws of acoustic propagation, remains below the threshold for cavitation, which in water at 500 kHz is approximately 3 MPa (30 bar). Cavitation, or bubble formation by acoustic rupture of the molecular potentials that bind water as a liquid, generates destructive shock waves when the bubbles collapse, and this is well known to cause indiscriminate mechanical disruption such as is found in lithotripsy. An aspect described herein is to adjust the geometry, excitation, and operating frequency to provide high cycle mechanical compression and tension on the membrane without exceeding the cavitation threshold in any part of the treated area.

The acoustic pressure field is applied to the ensemble of healthy tissues and pathogens using piezoelectric transducers and driving electrical waveforms that are broadly adjustable using existing materials and devices. For example, fixed geometry probes are available from Philips (Philips N.A., LLC, Cambridge, Mass.) spanning frequencies in the MHz range such as the 288 linear element model L18-5 for steerable pulsed Doppler imaging, or the curved array model C10-3v with a 163° field of view for various medical diagnostic applications. Alternative transducers for spot welding, non-destructive material evaluation with angle beam or shear wave transducers, and phased array probes are available from Olympus (Olympus Corporation, Breinigsville, Pa.). Another source of acoustic transducers is Sonic Concepts (Sonic Concepts, Inc., Bothell, Wash.), who provide pulse-echo single line transducers, linear transducers, Doppler arrays, and other underwater configurations for sonar.

More recently, stretchable, flexible transducers have evolved for the purpose of ultrasound imaging, as described by Hu et al., U.S. Pat. App. Publication No. US 2019, 0328354 A1; and see Hu et al., *Science Advances* 4: eaar3979 (2018), both of which are incorporated by reference for the teachings thereof. FIG. 15A-H are extracted from US 2019/0328354 A1 (presented therein as FIG. 1A-H) and illustrate the wide variety of shapes over which the flexible transducer arrays can form with low impedance acoustic contact. Moreover, finite element analyses of acoustic wave propagation from these transducer arrays through complex tissues make this configuration appropriate for focused access to both surface and interior spaces of a patient treated according to the present invention.

Figure 15A:
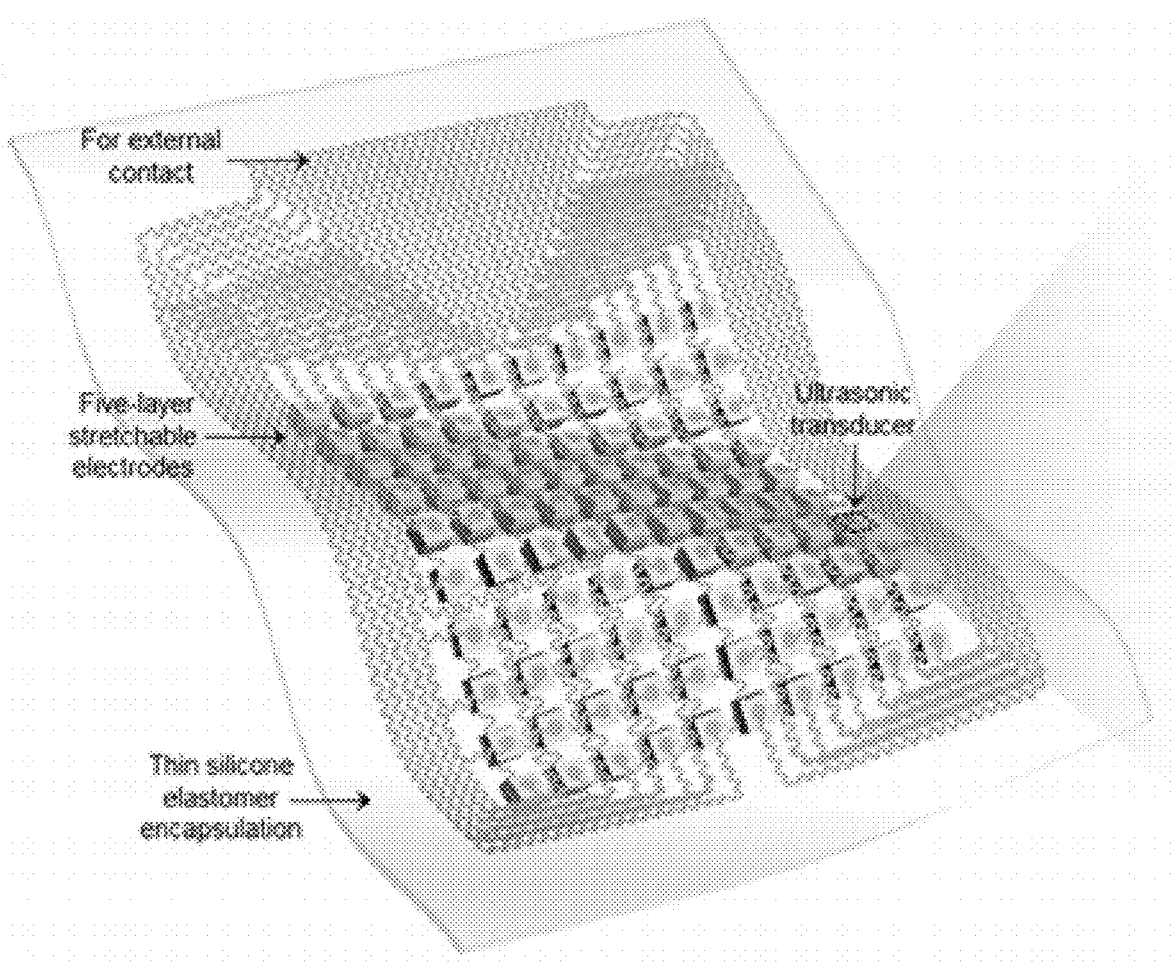
FIG. 15A-H schematically illustrate the design of a stretchable ultrasonic transducer array.

One example of a stretchable ultrasonic transducer array is shown in FIG. 15A. The piezoelectric transducers are arranged in a 10×10 array, connected by an "island-bridge" structured matrix. Each island hosts a rigid transducer element. The wavy bridges can unfold to accommodate the externally applied strain, with limited strain on the components themselves. Therefore, the matrix is rigid locally but soft globally. Each transducer element in the array is individually addressable. The soft probe can consequently reconstruct the target morphology in multi-section images.

Figure 15B:
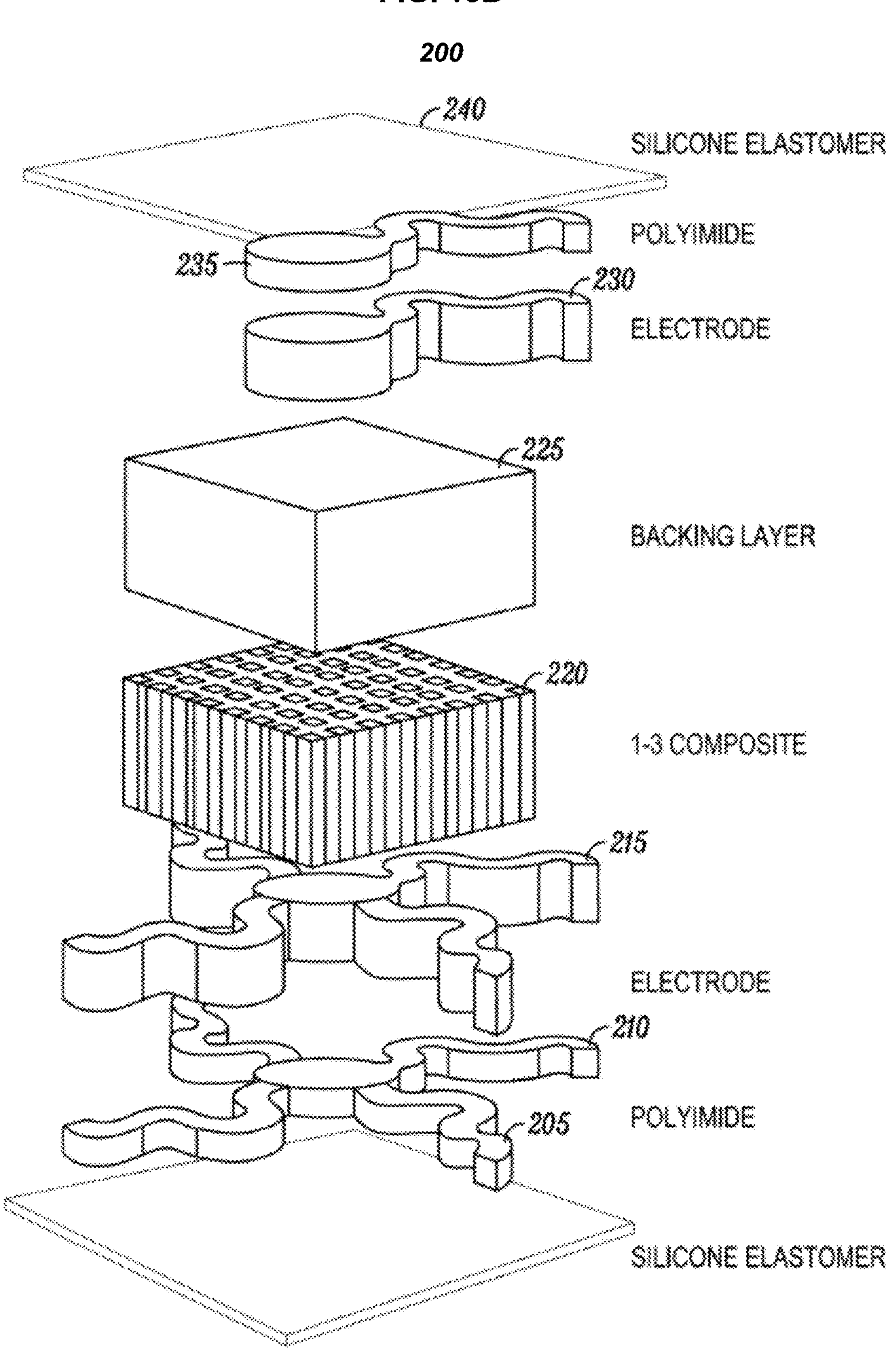

FIG. 15B shows the exploded view of one transducer element (200). In this example, both the substrate and superstrate are silicone elastomer thin films, whose low modulus (~70 kPa) and large stretchability (~900%) offer an extremely compliant platform to accommodate a diverse class of building blocks, such as piezoelectric elements, metal interconnects, backing layers, and solder paste. More specifically, in this example the transducer element (200) includes a substrate (205), a first patterned bilayer that includes a polymide layer (210) and an electrode (215), a piezoelectric electric (220), a backing layer (225), a second patterned bilayer that includes a polymide layer (235) and an electrode (230), and a superstrate (240). The elastomer substrate and superstrate thickness are 15 μm to provide both high acoustic performance and mechanical robustness of the device. The islands and bridges are formed from patterned bilayers of Cu (20 μm)/polyimide (PI, 2 μm). The PI layer greatly enhances the bonding strength between the Cu and elastomer.

Figure 15C:
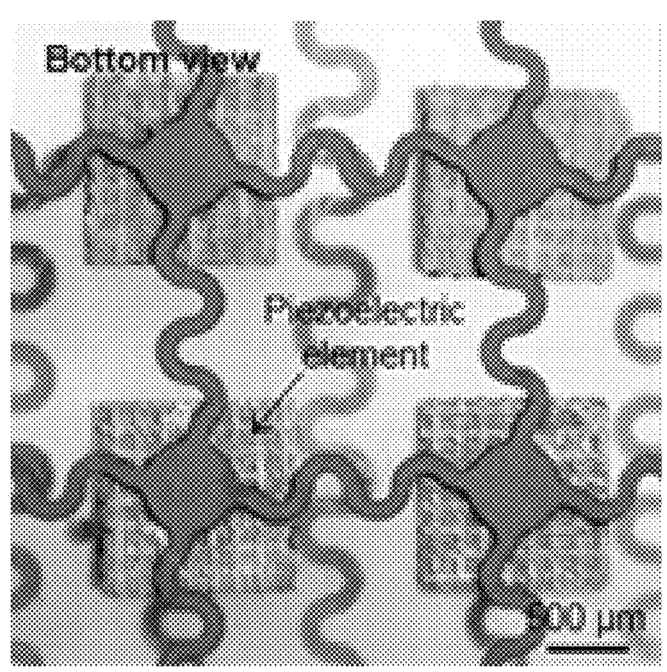
Figure 15D:
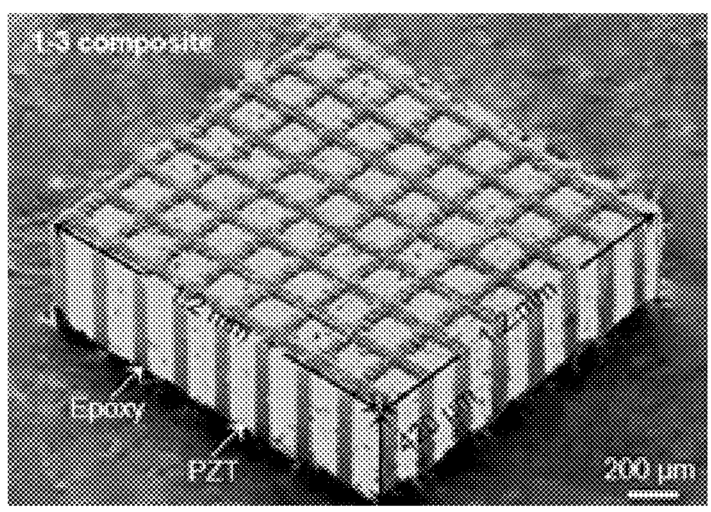
Figure 15E:
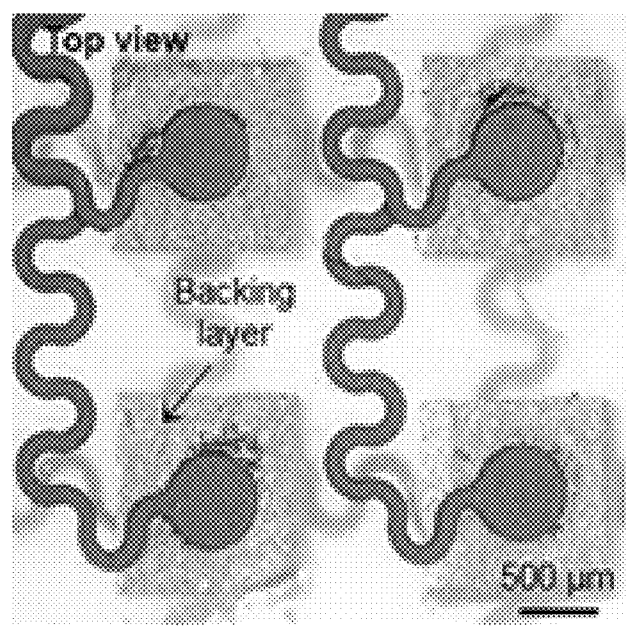

In one embodiment, piezoelectric 1-3 composites are chosen as the active material of the transducers. Piezoelectric 1-3 composites are polymer composites with 1-3 connectivity consisting of length-extensional piezoelectric elements embedded in a passive matrix. See e.g., Lee et al., *IEEE Trans. Ultrason. Ferroelectr. Freq. Control.* 59(9): 1969-1975 (2012), which is incorporated by reference herein for such teachings. FIG. 15C shows an optical image of a bottom view four transducer elements and FIG. 15D an SEM image of a piezoelectric 1-3 composite. Compared with an isotropic PZT, the anisotropic 1-3 composites have superior electromechanical coupling coefficients (thickness mode) that convert the majority of electric energy to vibration energy. In addition, the surrounding epoxy filler effectively suppresses transverse vibrations of PZT pillars, leading to enhanced longitudinal waves that go into the targeted objects. As seen in the optical image of FIG. 15E, the backing layer (225) effectively dampens ringing effects (excessive vibrations) of the piezoelectrics, which shortens spatial pulse lengths, and broadens the bandwidth and thus improves the image axial resolution. Silver epoxy and solder paste are used to build robust and electrically conductive interfaces of 1-3 composite/backing layer and 1-3 composite/metal electrode, respectively. Because of the close acoustic impedances of 1-3 composite (~20 Mrayl) and the targets to be tested (Al, ~18 Mrayl), the matching layer is not necessary in this study.

On the one hand, the pitch between adjacent transducer elements should be small to reduce side lobe and grating lobe artifacts in the acquired images. On the other hand, sufficient space between elements should be allocated to the serpentine interconnects for sufficient stretchability. In one embodiment, a pitch of 2.0 mm (1.2 mm×1.2 mm element footprint with a spacing of 0.8 mm between each column) is employed, which can achieve over 30% reversible stretchability. The high spatial resolution (~610 μm), negligible cross-talk level between adjacent elements (~−70 dB), and artifact-free images validates this pitch design. Within such limited footprints, the "island-bridge" electrode layout design is critical considering the large number of electrical connections needed for wiring the 10×10 array. An active multiplexing matrix under the ultrasound transducers could be a potential solution. However, the structural support materials introduced by the multiplexing matrix will negatively impact the device stretchability. Multilayered electrodes have been demonstrated, but the electrode design, passive dielectrics, and the substrate make the devices only flexible but not stretchable. To individually address the transducer elements, a minimum of electrodes with a common ground electrode is needed. It is very challenging to place this large number of electrodes within limited footprints using conventional single layer designs.

Figure 15F:
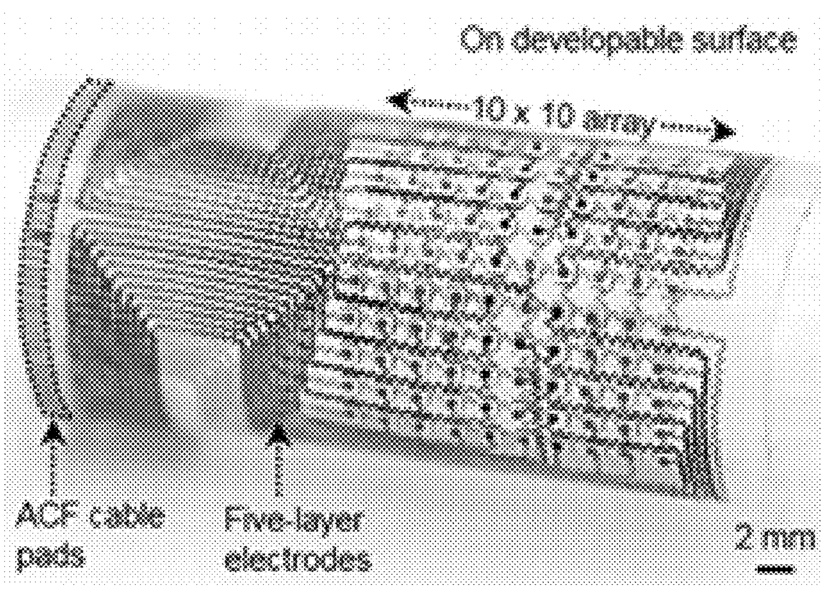
Figure 15G:
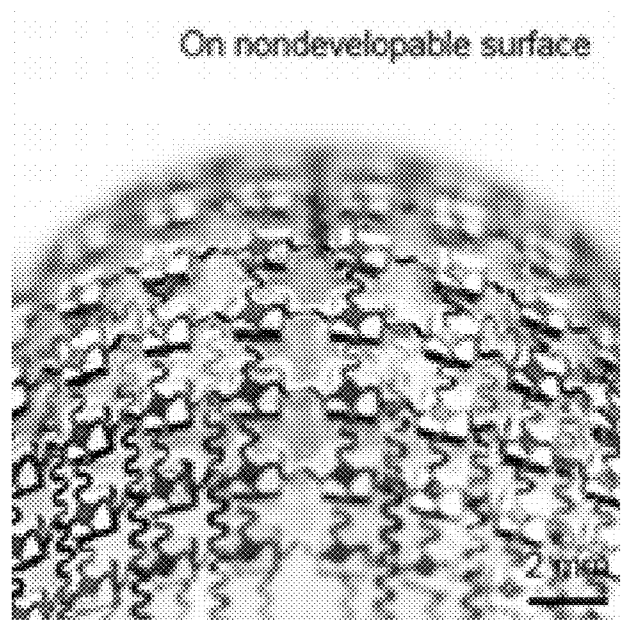
Figure 15H:
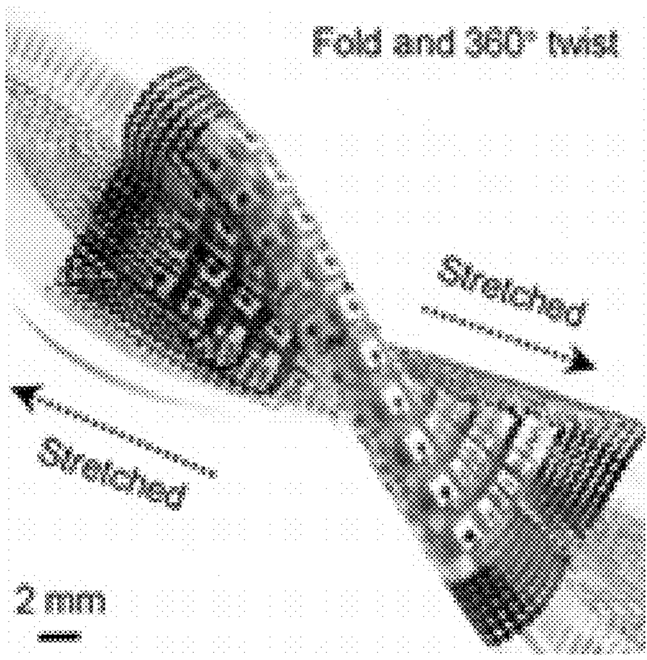

Compared with microfabrication methods by lithography and etching, which requires sophisticated fabrication processes, chemicals, shadow masks, and a cleanroom environment, laser ablation is time efficient, low cost, and offers high throughput. The as-fabricated final device is seen in FIG. 15F-H, which highlights the excellent mechanical properties when conforming to developable (cylindrical) and non-developable (spherical) surfaces, and under mixed modes of folding, stretching, and twisting. In particular, FIG. 15F-H respectively show optical images of the stretchable device when bent around a developable surface, wrapped on a non-developable surface, and in a mixed mode of folding, stretching, and twisting, showing its mechanical robustness.

Any of the transducer configurations are amenable to analysis of acoustic propagation by the finite element computational methods described herein.

Figure 3A:
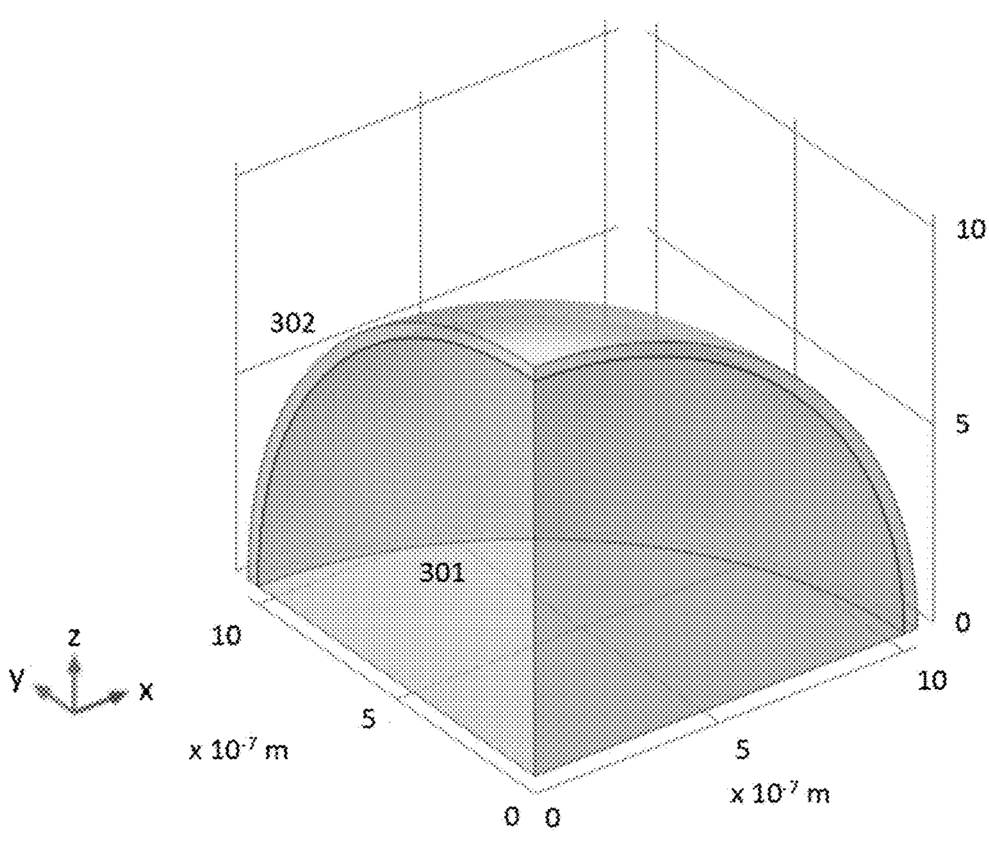
FIG. 3A-C show one octant of a simplified spherical model of a pathogen (FIG. 3A) with internal constituents (301) and a membrane (302) under cyclic external pressure conditions.
Figure 3B:
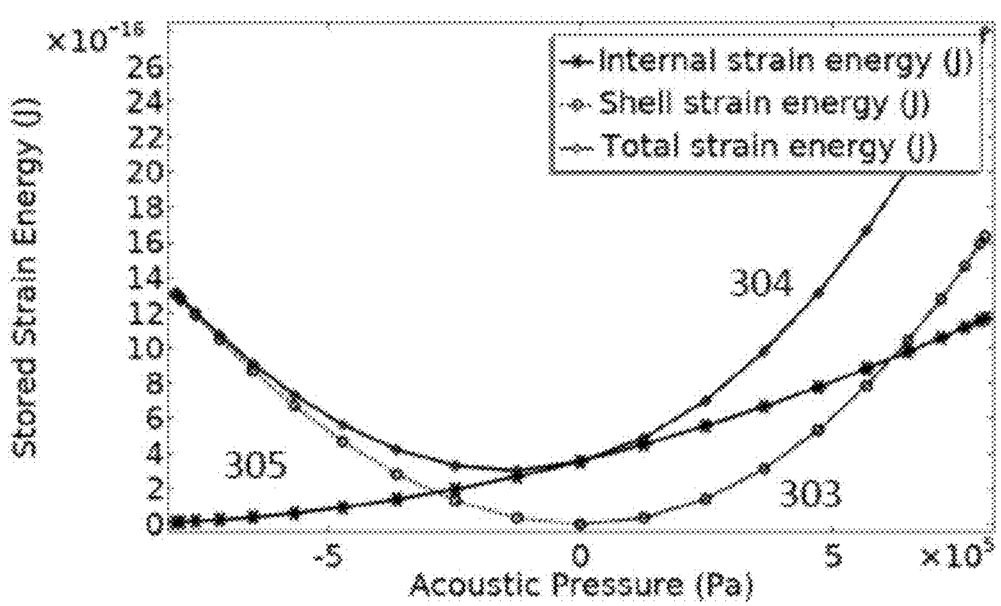
Figure 3C:
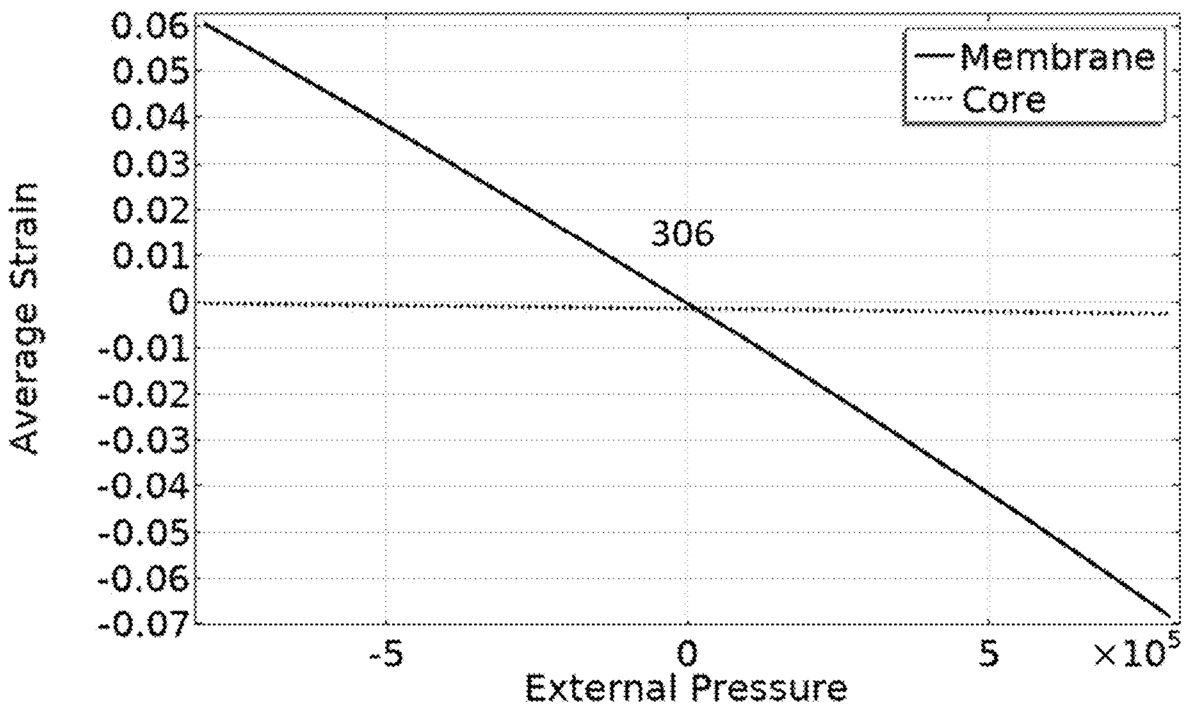

The mechanical stresses and strains that result from sinusoidal fluctuations of the external pressure are evaluated using finite element methods. A simplified isotropic membrane surrounding a volume of fluid whose dimensions and mechanical properties are representative of the bacterium *Staphylococcus aureus* is displayed in FIG. 3A. The spherical cellular constituents (301) and membrane (302) are displayed in a subset of one octant centered on the origin. The internal material starts at a pressure of 1 MPa (10 atmospheres) and the acoustic pressure is stepped from −800 kPa to 800 kPa from the ambient of 100 kPa. At 0 acoustic pressure there is strain energy stored in the internal fluid (301) to account for the internal hydrostatic pressure of the pathogen. As the external pressure drops compressive and tensile strain in the membrane results as the strain from internal pressure on the core is relaxed, so most of the strain energy, peaking at $1.02\times10^{-14}$ J ($=8*13\times10^{-16}$ J) —the energy plotted is for one of eight octants of the structure), is taken up in the membrane. FIG. 3B. Proceeding to the positive pressure side both the core and membrane are compressed, with the membrane taking up more than half of the total strain energy. Referring to FIG. 3C, the membrane strain is 6-7% while that of the core is barely perceptible at this scale. The membrane comprises only 11% of the volume of the core so it has 14-times the latter's strain energy density. In other words, the strain and stress in this elementary model of a pathogen are focused on the relatively compliant membrane rather than the relatively rigid contents that the membranes surround.

The detailed interaction of an acoustic field with pathogens and normal cells is much more complex. For example, bacterial membranes are at least orthotropic rather than isotropic, their structure is heterogeneous rather than homogeneous, and they have active pores that enable exchange of material with their environment. Nevertheless, these complex structures are vulnerable to high cycle fatigue that compromises their integrity. Typical yield or fracture strengths under cyclic loading conditions for most materials are 50-75% of the corresponding static values. Moreover, the membranes of pathogens have microstructural features such as ion pumps to maintain osmotic pressure, pores to facilitate transport of nutrients in and waste out of the cytoplasm, and various components that may be damaged or destroyed by repeated compression, tension, and shear within the membrane.

Figure 4:
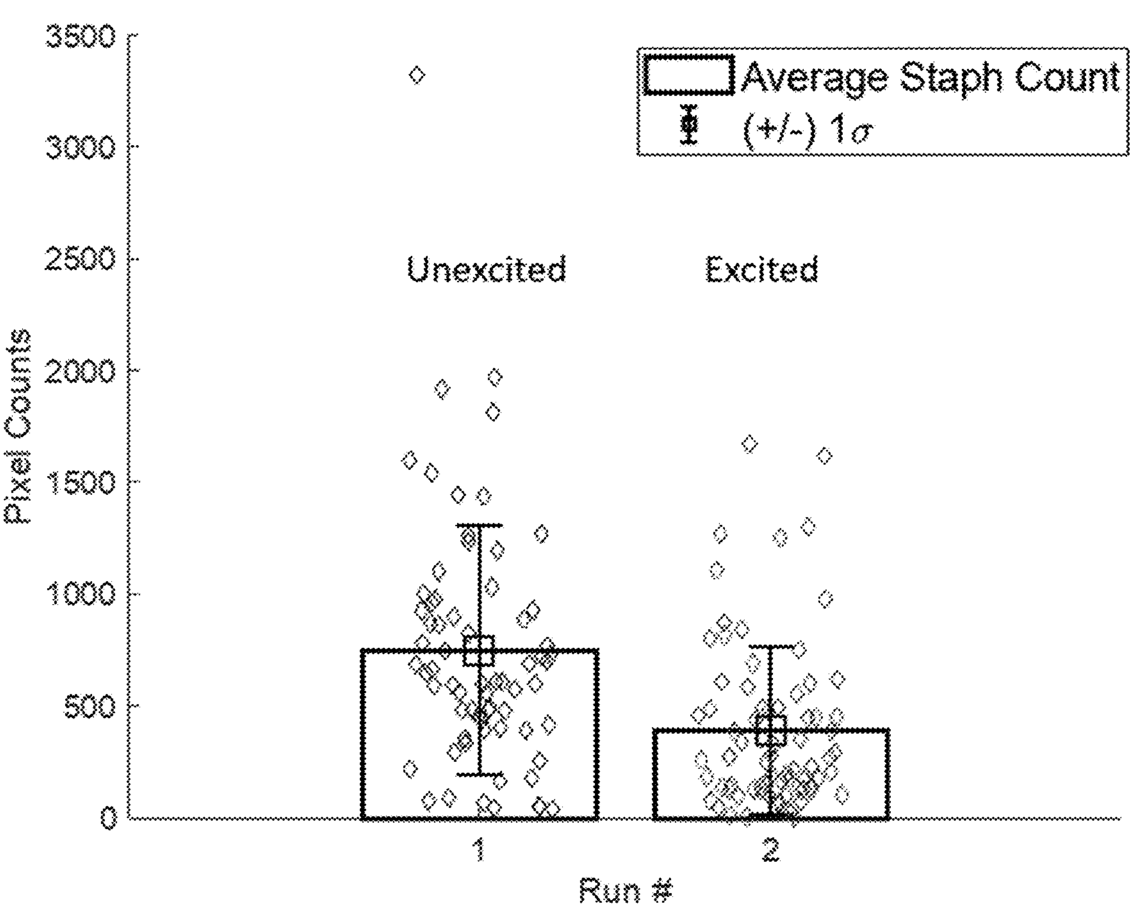
FIG. 4 shows populations of *S. aureus* without (Run 1) and with (Run 2) acoustic irradiation.
Figure 5:
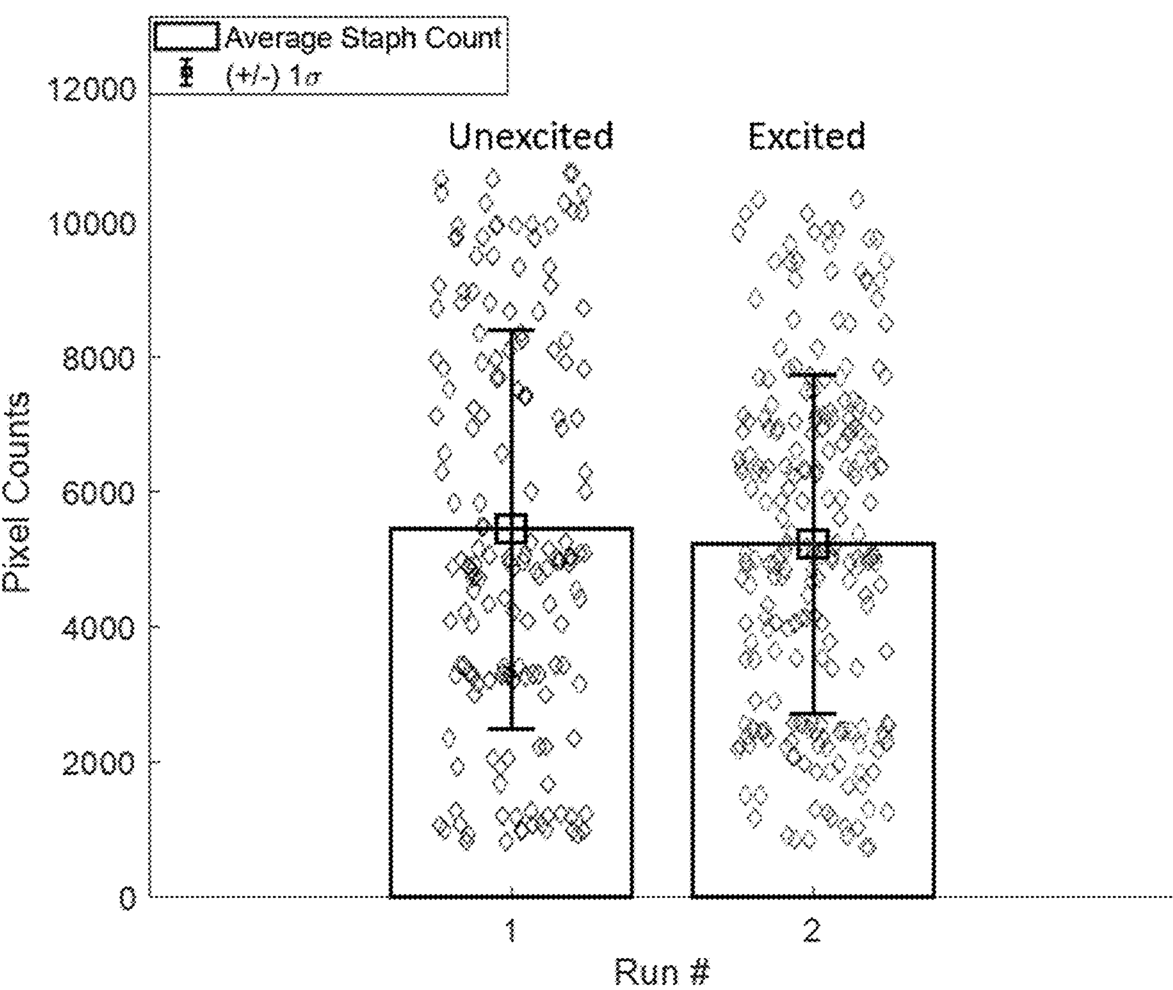
FIG. 5 shows populations of *S. aureus* with and without acoustically treated neutrophils.

One embodiment described herein is a method for targets compromise of an in vitro mixture of green fluorescing *Staphylococcus aureus*. Using the geometry and excitation source set forth in FIG. 2, these samples are irradiated with source displacements of 25 nm at 500 kHz in 50 bursts of 1000 cycles for a total of 50,000 cycles of compression and tension. The populations of bacteria were assayed by fluorescence imaging and image processing using standard MATLAB (Math Works, Natick, Mass.) software after 100-140 minutes of incubation. Referring to FIG. 4, a total of 142 replications shows a significant drop in the growth rates of the irradiated bacteria. In another experiment, samples of healthy human neutrophils were exposed to identical acoustic irradiation. Neutrophils ingest bacteria so bacterial populations are attenuated by them. See Irimia et al., *Methods Cell Biol.* 147: 93-107 (2018). FIG. 5 shows populations of *S. aureus* between 100 and 140 minutes following the addition of unexcited and acoustically excited neutrophils from the same donor. The motility and bacteria-neutralizing potency of the neutrophils is unaffected by acoustic excitation under the same conditions that independently compromise the integrity of bacteria. In other words, the neutrophils are unaffected when subjected to the same 50,000 cycles of acoustic fatigue that damage the pathogens.

Summarizing, selection of a frequency (500 kHz) and a transducer amplitude (25 nm) for acoustic excitation of this in vitro mixture of normal and pathogenic cells resulted in selective degradation of the pathogen with no change to the number, motility, or immunological potency of the normal mammalian cells.

Figure 6:
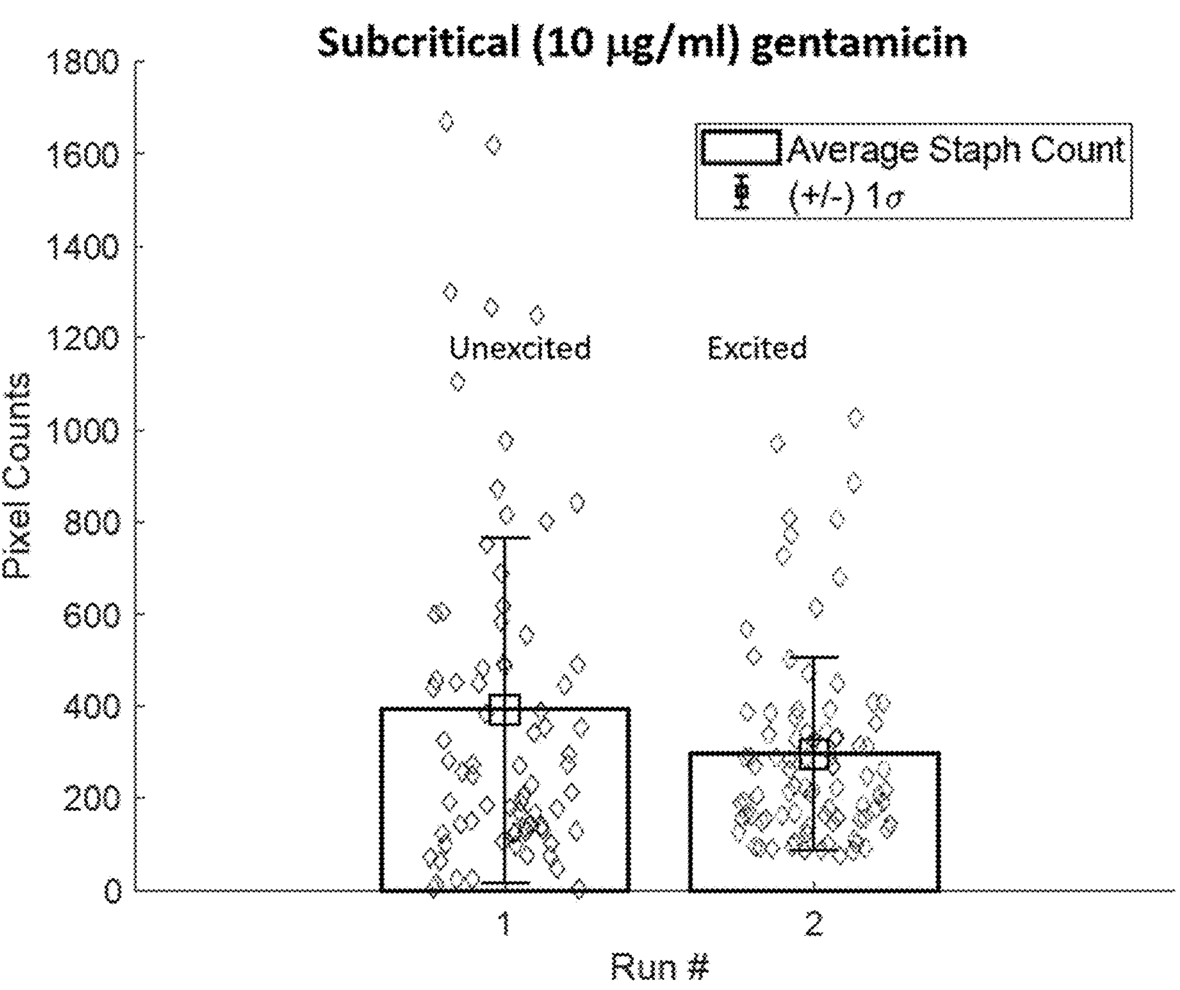
FIG. 6 shows populations of *S. aureus* treated with 10 μg/mL gentamicin without (Run 1) and with (Run 2) acoustic excitation.

Another embodiment of the method involves acoustic synergy with traditional pharmaceutical antibiotics. Inoculants of *S. aureus* were acoustically stimulated as described previously, with populations tallied in a total of 164 replications after two hours. 89 of these replications included 10 μg/mL of the antibiotic gentamicin, a concentration that produces no measurable impact on *S. aureus* viability in the absence of acoustic treatment. Referring to FIG. 6, gentamicin at normally ineffective doses reduces both the average population and its variability. One mechanism behind this observation is that high cycle acoustic stimulation of the pathogen's membranes increases their permeability to gentamicin, potentially providing opportunities to combat antibiotic resistance with FDA approved antibiotics whose potency is waning because of pathogen evolution.

Figure 7A:
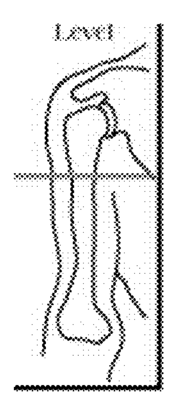
Figure 7A:
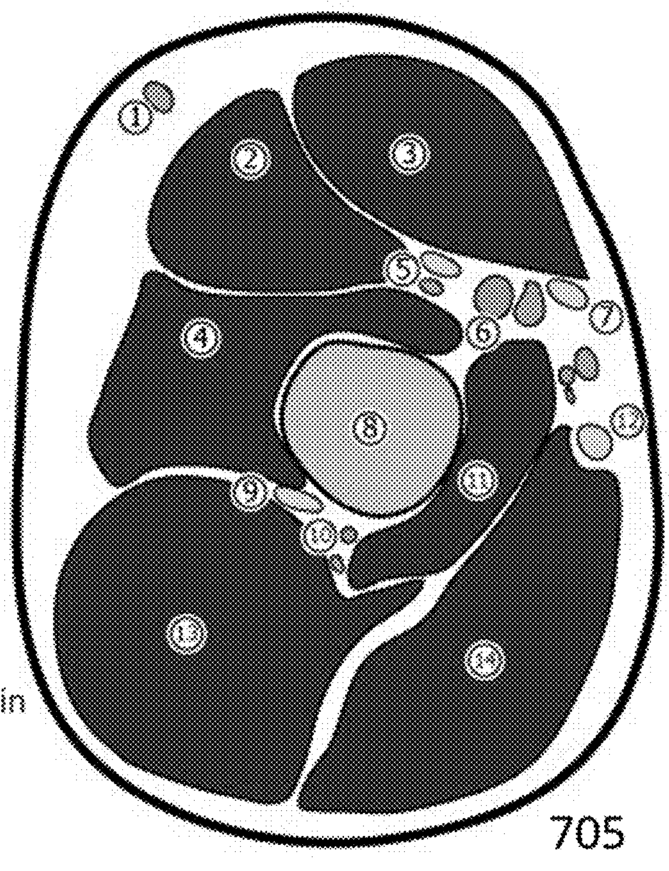
Figure 7B:
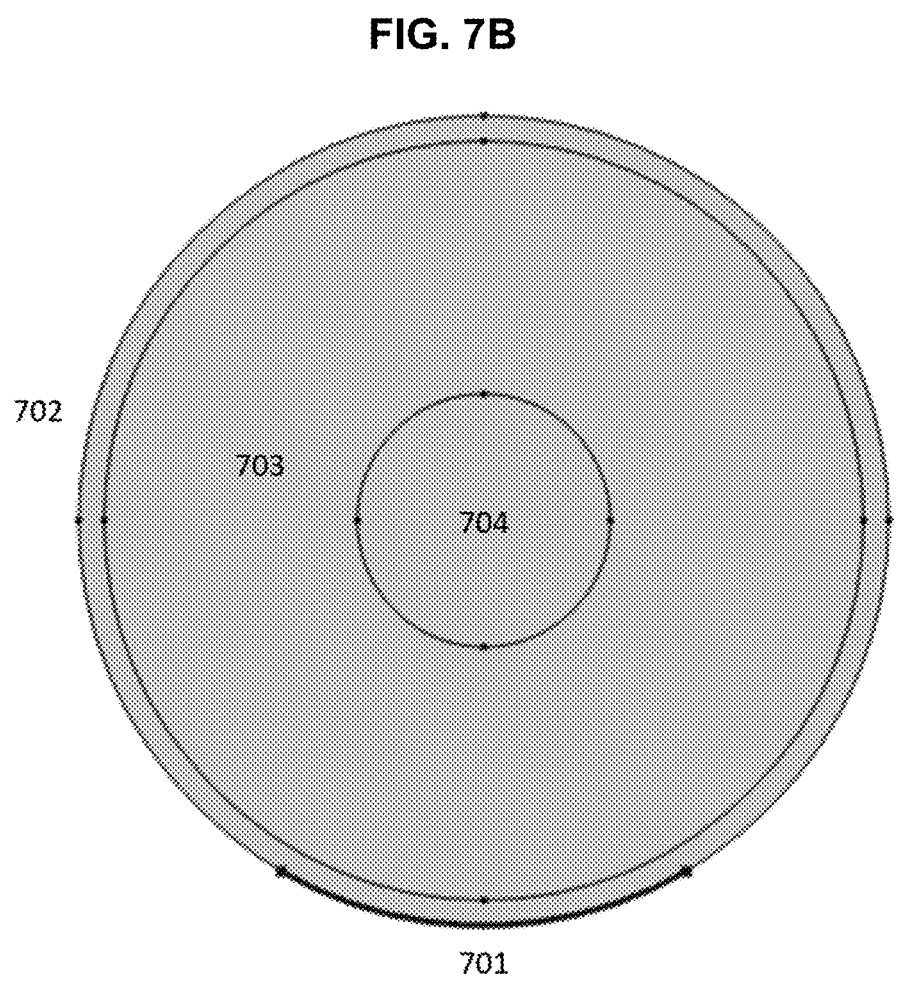
Figure 8:
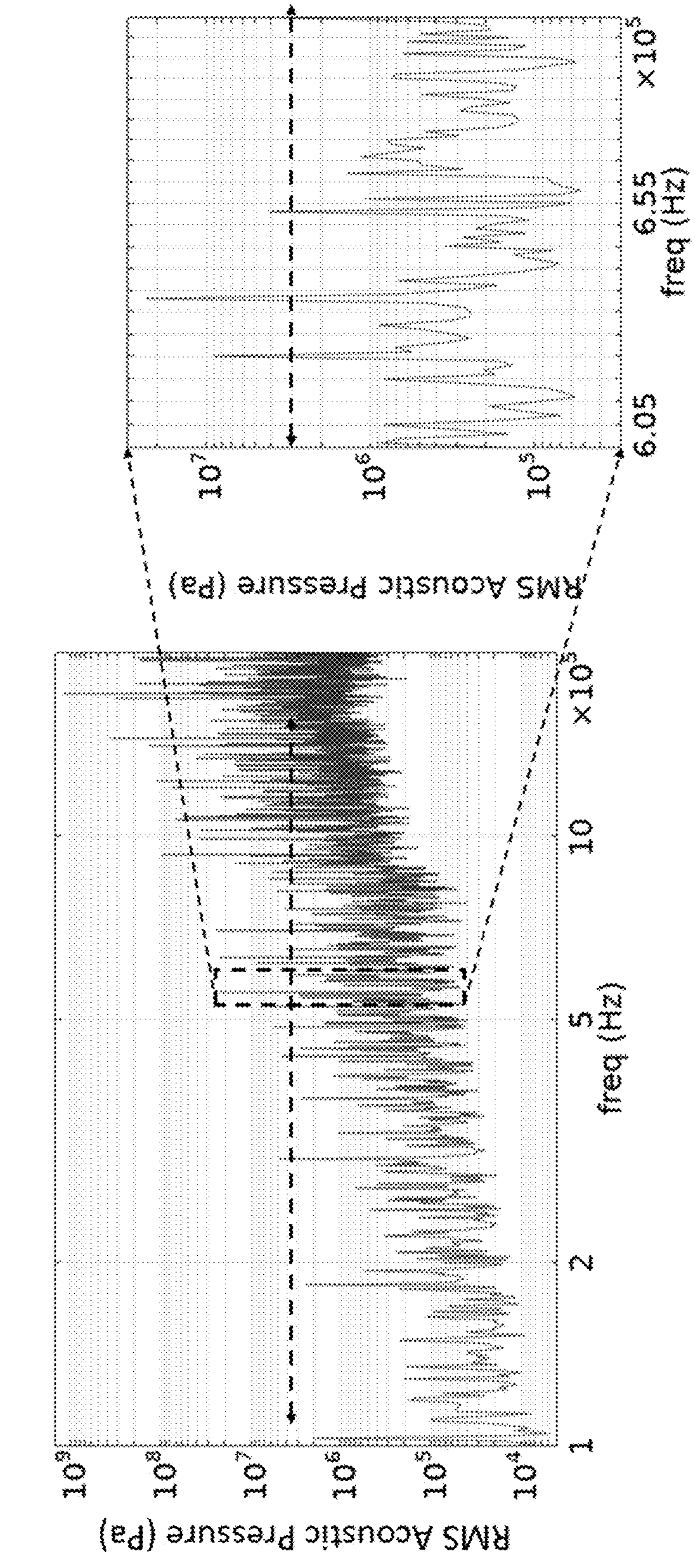
FIG. 8 shows the RMS acoustic pressure as a function of frequency for excitation conditions in FIG. 7 from 0.1-2 MHz with an expanded view from 600-700 kHz.

Another embodiment of the method illustrates the use of acoustic compromise of pathogens in bone. FIG. 7A displays a cross-section of the upper extremity (705) and a simplified cross-sectional model of bone embedded in muscle and surrounded by skin. Actual geometries measured using axial tomography or magnetic resonance images of an individual patient's afflicted area could be substituted for this simplified geometry and could include blood vessels, cartilage, teeth, and other tissues whose acoustic properties differ from those of their surroundings, as is known to those practiced in the art of biophysics and finite element analysis. The speeds of sound in these media differ, causing internal reflection and refraction that is evaluated as a function of transducer shape, amplitude, and orientation. FIG. 7B illustrates a curved piezoelectric transducer (701) in intimate contact with skin (702) over a sixty-degree arc. Acoustic waves launched by 10 nm sinusoidal displacement of this transducer generate acoustic waves that are approximately focused on the infected bone (704) in this example. The pressure distribution into skin, muscle (703), and the infected bone volumes was computed as a function of transducer amplitude and excitation frequency at 1 kHz intervals from 100 kHz to 2 MHz. FIG. 8 displays the gradual increase in peak pressure as frequency increases, but closer examination reveals frequency ranges between 600 and 700 kHz where the pressure remains below the cavitation threshold of 3 MPa for this combination of amplitude, shape, and target medium.

Figure 9A:
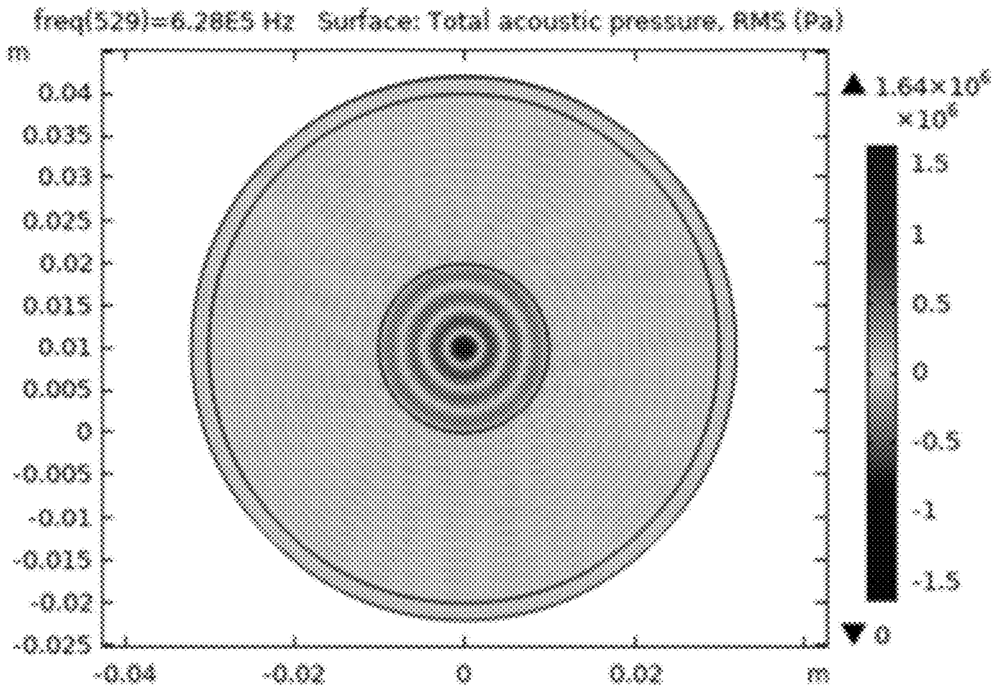
FIG. 9A-C show acoustic pressure distributions in the model limb of FIG. 7 at 628 kHz (FIG. 9A), 631 kHz (FIG. 9B), and 633 kHz (FIG. 9C).
Figure 9B:
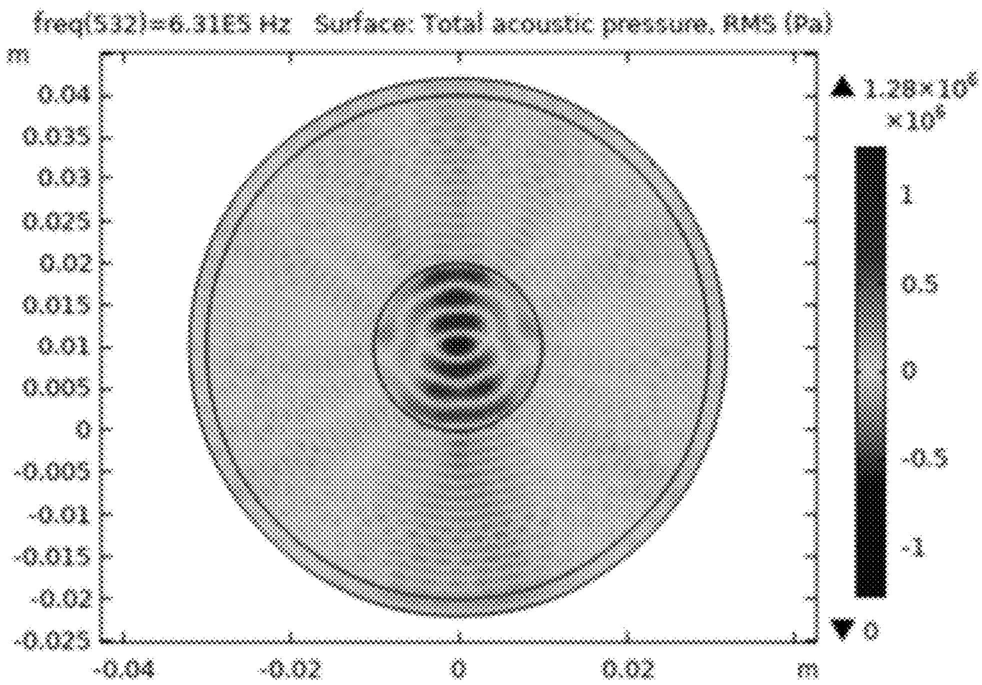
Figure 9C:
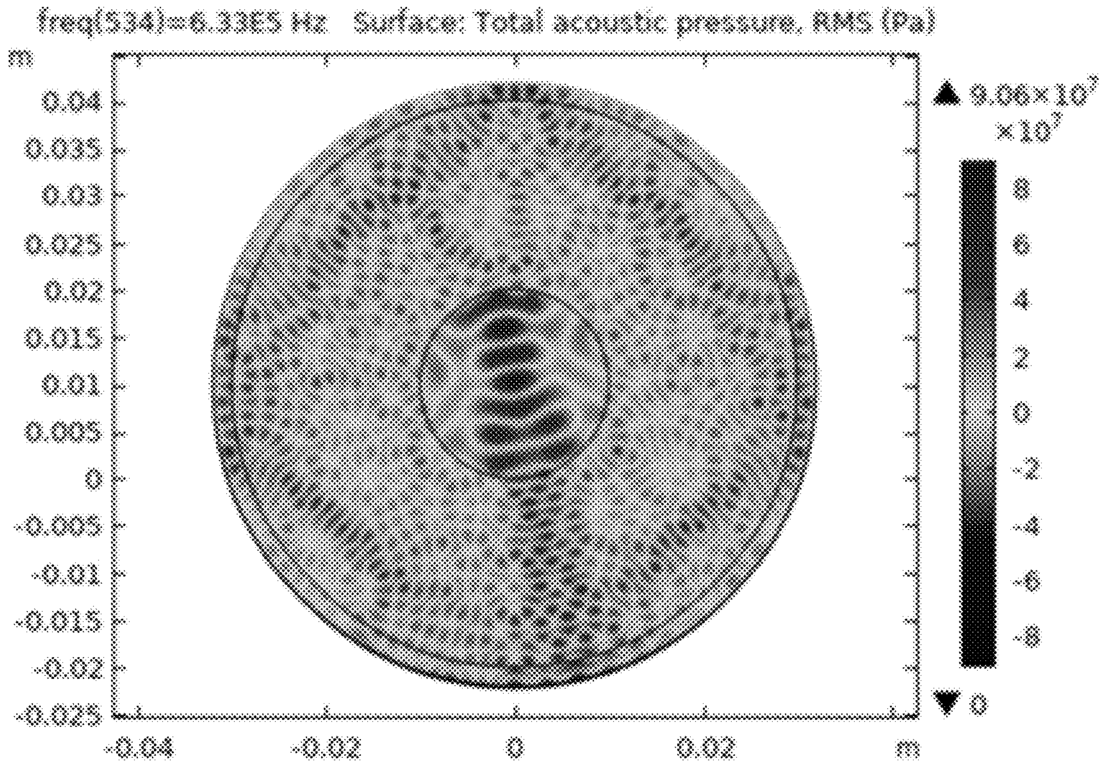
Figure 10A:
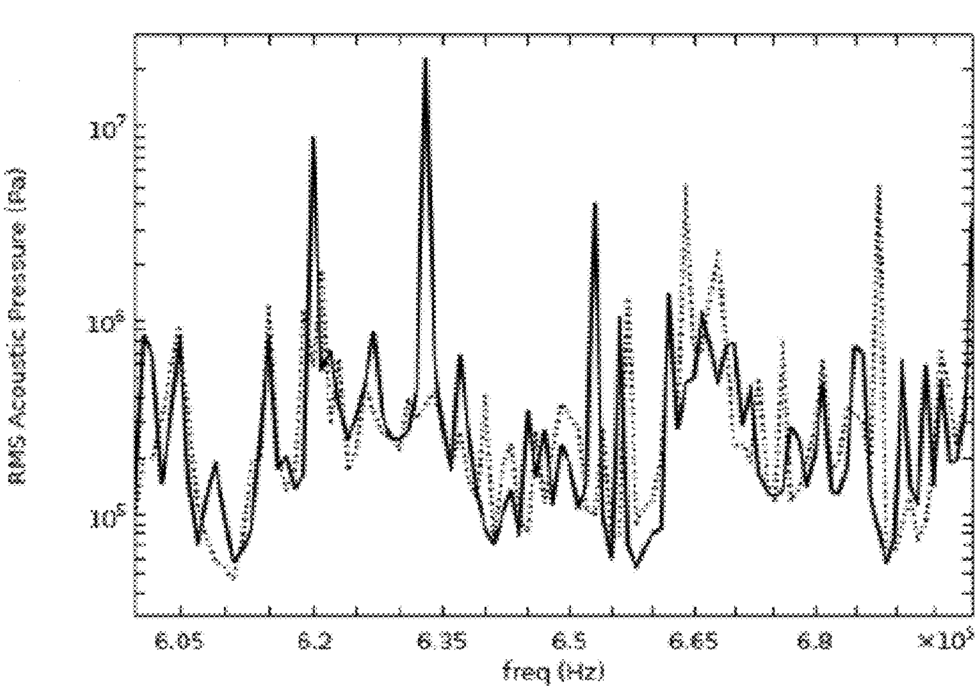
FIG. 10A-E show the RMS acoustic pressure (FIG. 10A) and its spatial distributions at 628 kHz (FIG. 10B), 631 kHz (FIG. 10C), and 633 kHz (FIG. 10D) for an asymmetric limb simulation (FIG. 10E) with a small bone (1001) added to the geometry described in FIG. 7.
Figure 10B:
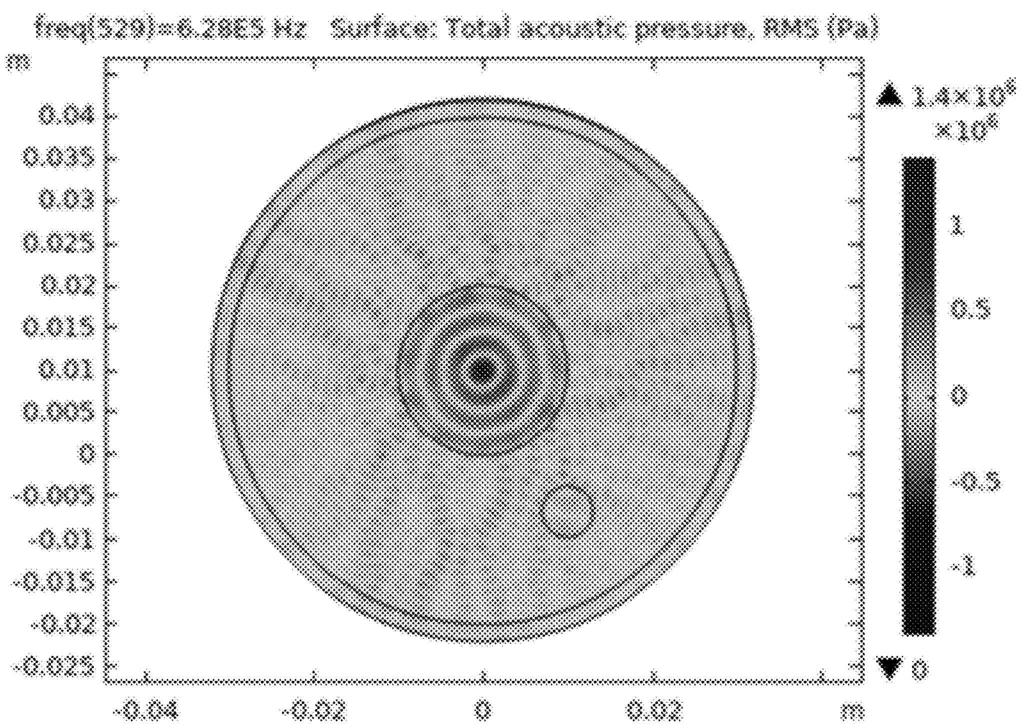
Figure 10C:
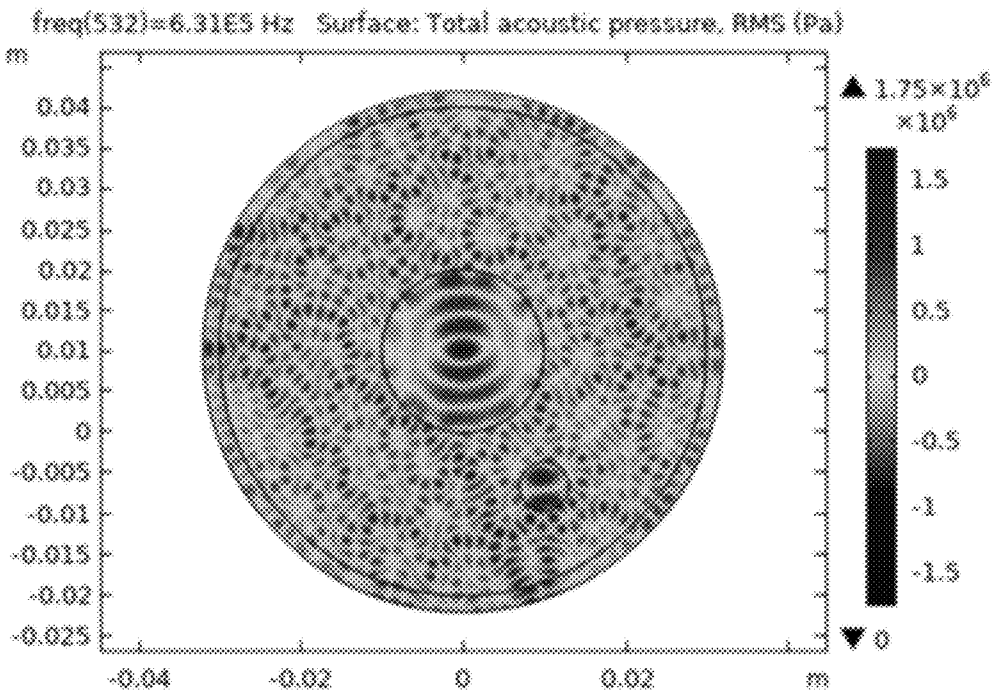
Figure 10D:
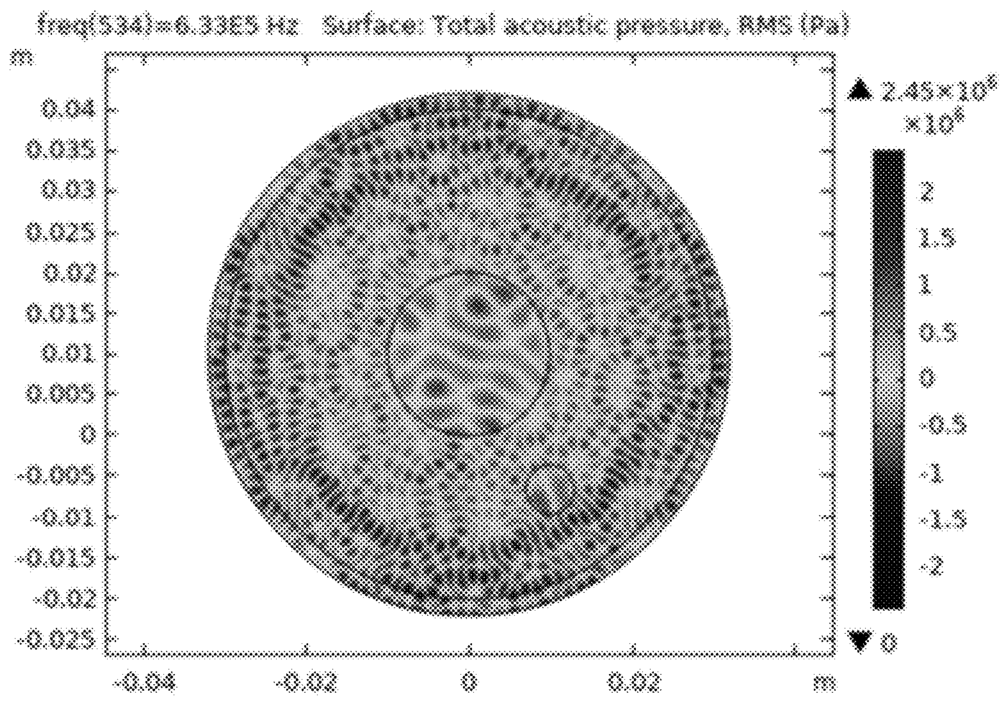
Figure 10E:
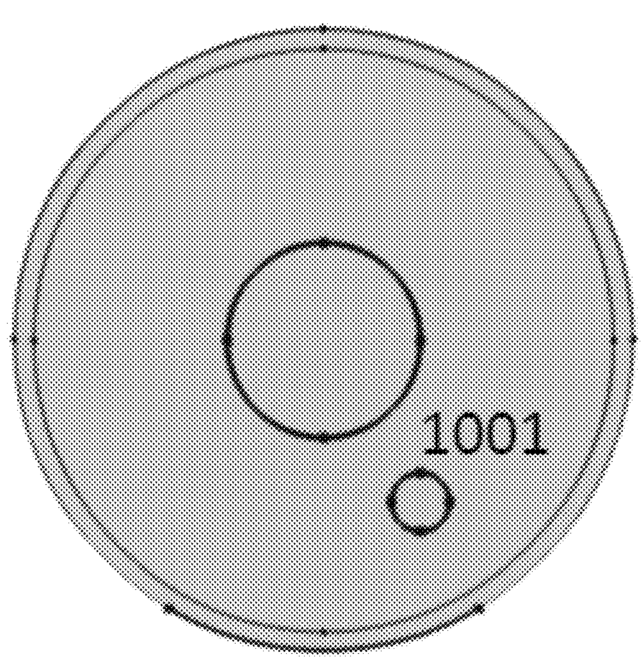
Figure 11A:
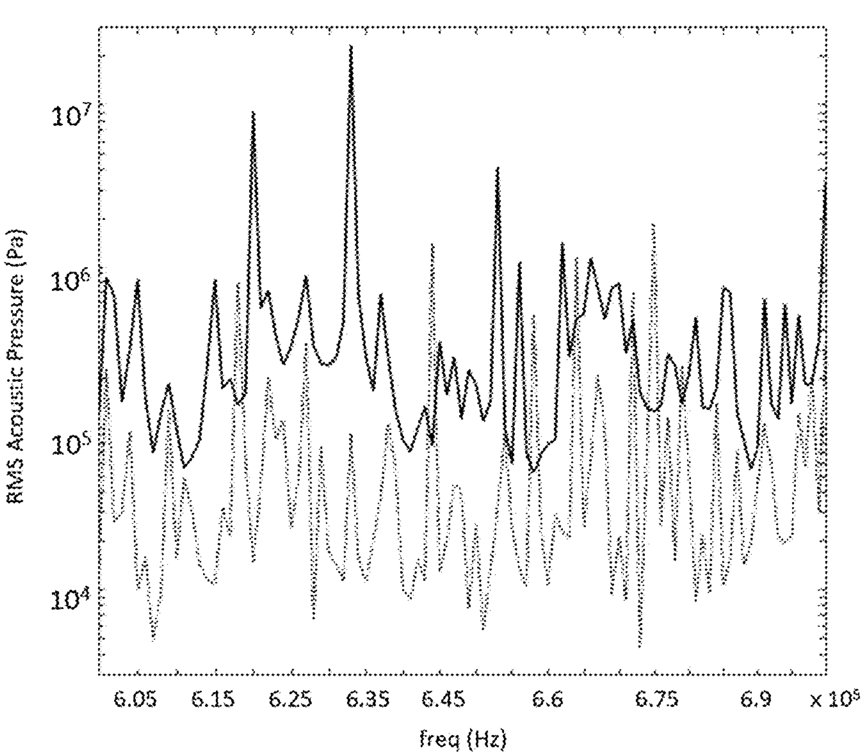
FIG. 11A-E show the RMS acoustic pressures (FIG. 11A-B) and its spatial distributions at 314 kHz (FIG. 11C), 316 kHz (FIG. 11D), and 320 kHz (FIG. 11E) in a model limb using acoustic stimulation of a stiff steel probe (1101) that is mechanically connected to the inner bone (1102), as illustrated in FIG. 11C.
Figure 11B:
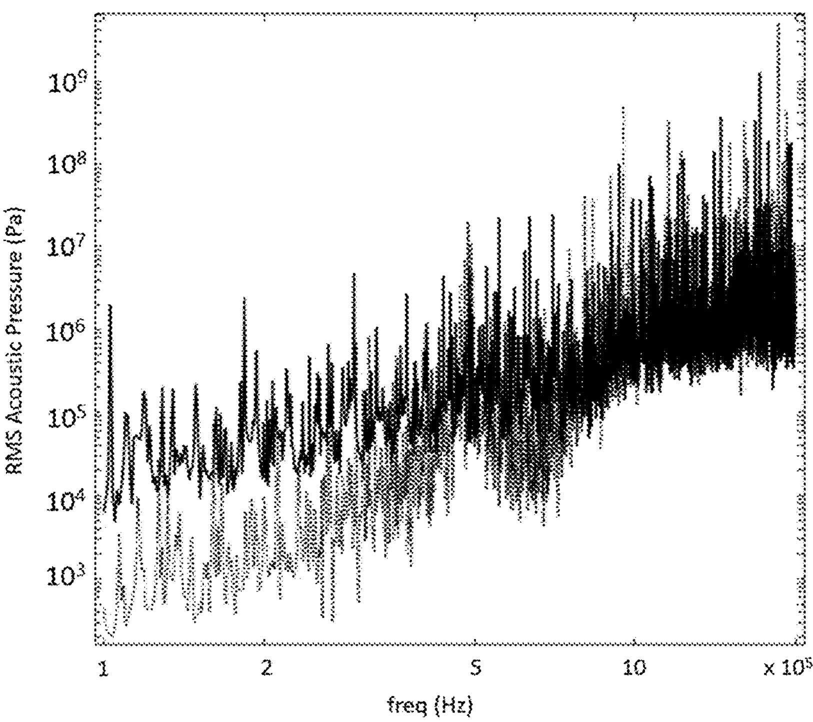
Figure 11C:
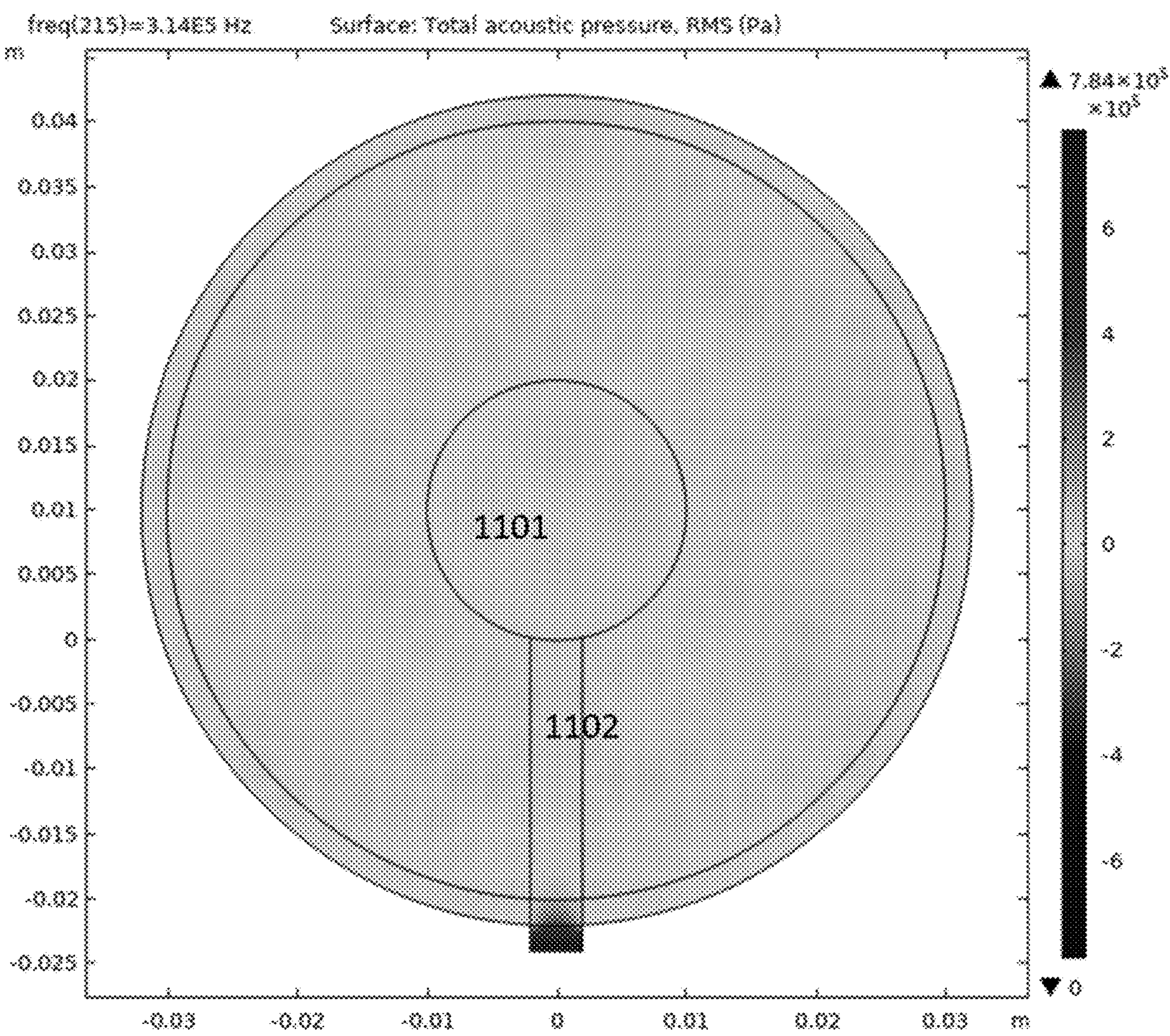
Figure 11D:
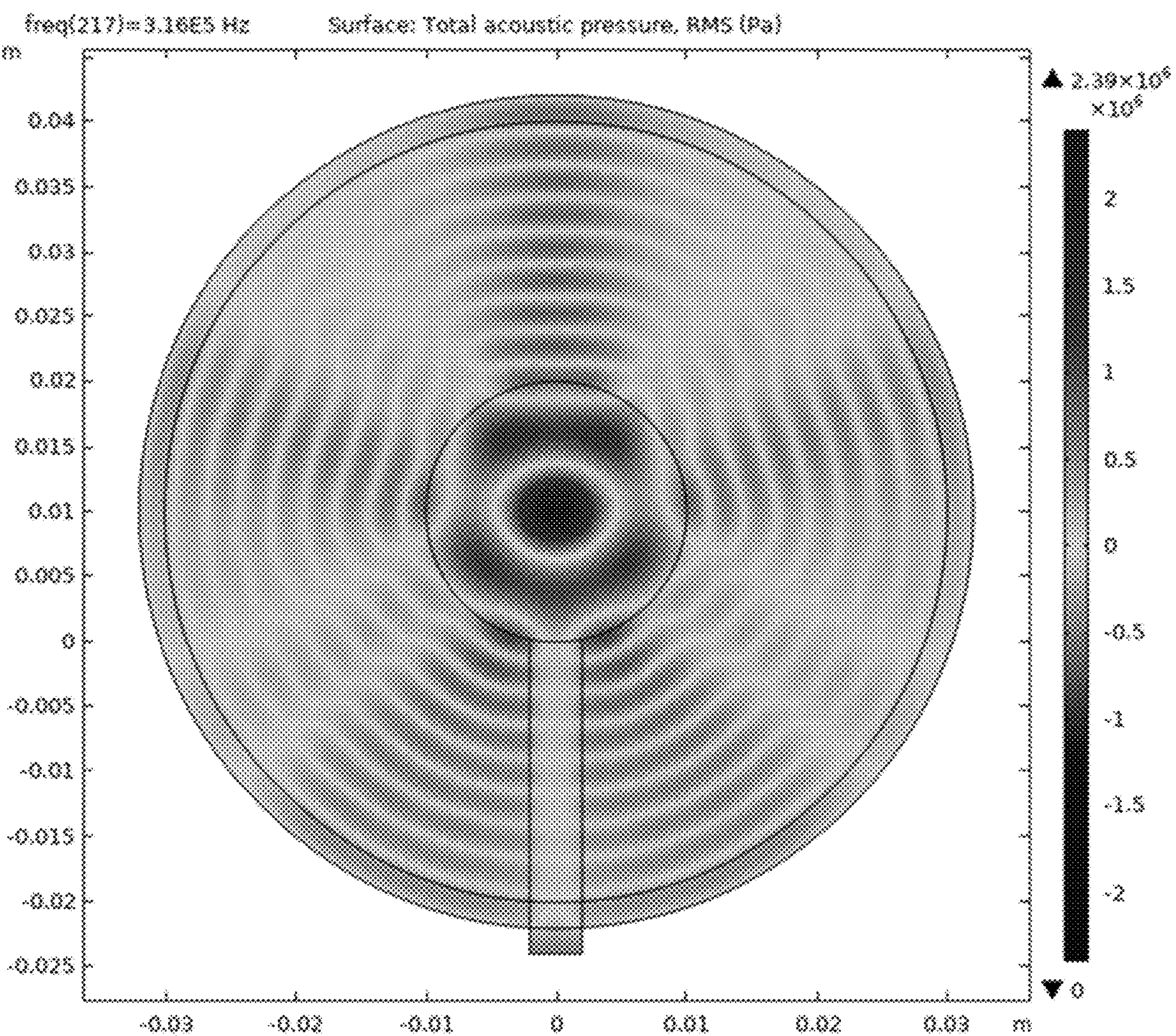
Figure 11E:
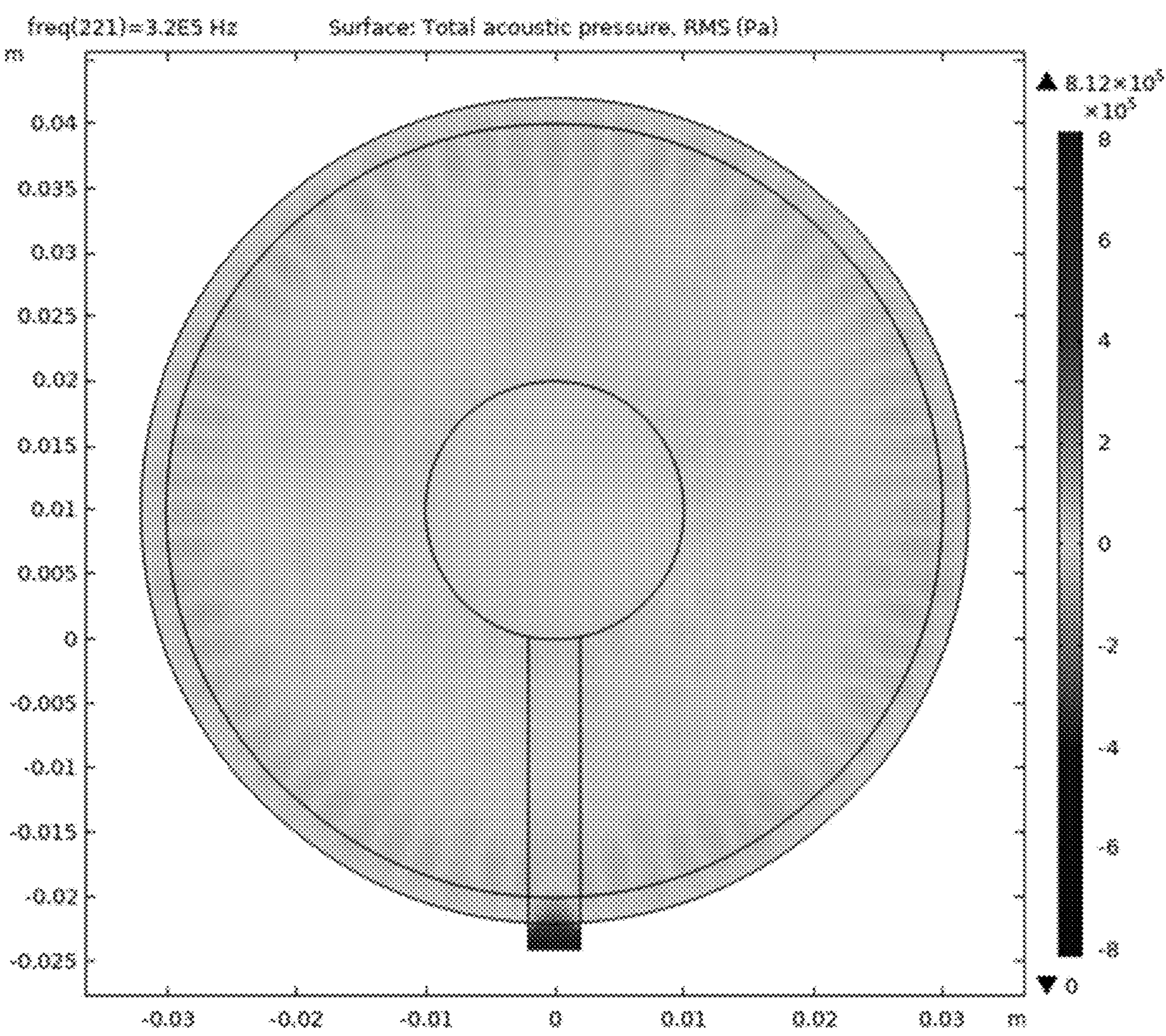

The importance of selecting transducer amplitude, frequency, and geometry is further understood referring to FIG. 9A-C, which displays the calculated root-mean-square pressure distributions within the bone, muscle, and skin regions for 10 nm transducer amplitudes at 628, 631, and 633 kHz. The pressures for the first two frequencies remain below 1.64 and 1.28 MPa, respectively, while the pressure peaks at over 90 MPa at 633 kHz. The spatial distribution of pressure within the infected bone is also seen to shift with applied frequency; this is useful to ensure complete exposure of the infected volume to high cycle acoustic fatigue. This aspect is important because infections within bone and at the bone-tissue interfaces are notoriously difficult to treat, often requiring invasive surgical access with its corresponding morbidities.

Another aspect of this embodiment is careful analysis of the infected tissue as it is found surrounded by other materials with differing acoustic properties. FIG. 10A-E illustrate this aspect by including a second, thinner bone (1001) between the edge of the transducer and the central bone. Using identical excitation conditions as were applied in FIG. 9 the frequency dependence of the acoustic pressures for this case, indicated by the dashed line, is redistributed over the 600-700 kHz range. Furthermore, the peak values of acoustic pressure have changed slightly at 628 and 631 kHz and quite dramatically from 90 to 2.45 MPa at 633 kHz. The spatial distributions of acoustic pressure are also affected by this more complex asymmetric geometry. Shifting the excitation from 628 kHz to 631 kHz qualitatively changes the pressure in the smaller diameter bone while providing about the same pressure profile to the larger bone region. As is clear from these examples, including other tissue types, geometries, and transducer configurations will alter the acoustic pressure profiles in manners that are straightforwardly calculated by those practiced in the art of acoustic modeling.

Figure 12A:
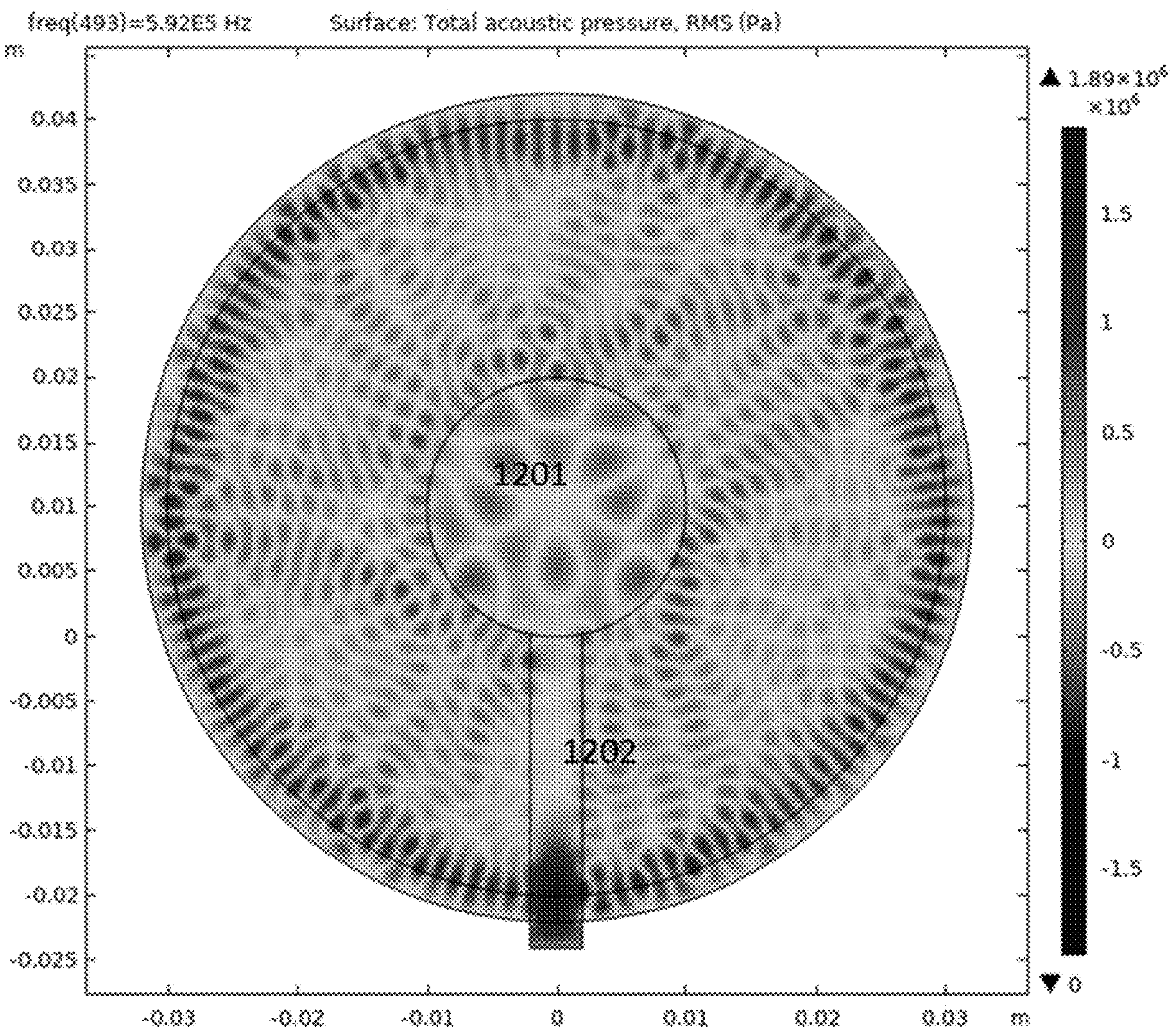
FIG. 12A-B show pressure distributions at 592 kHz (FIG. 12A) and 582 kHz (FIG. 12B) illustrating the controlled distribution of power at the muscle-skin interface or within the muscle itself.
Figure 12B:
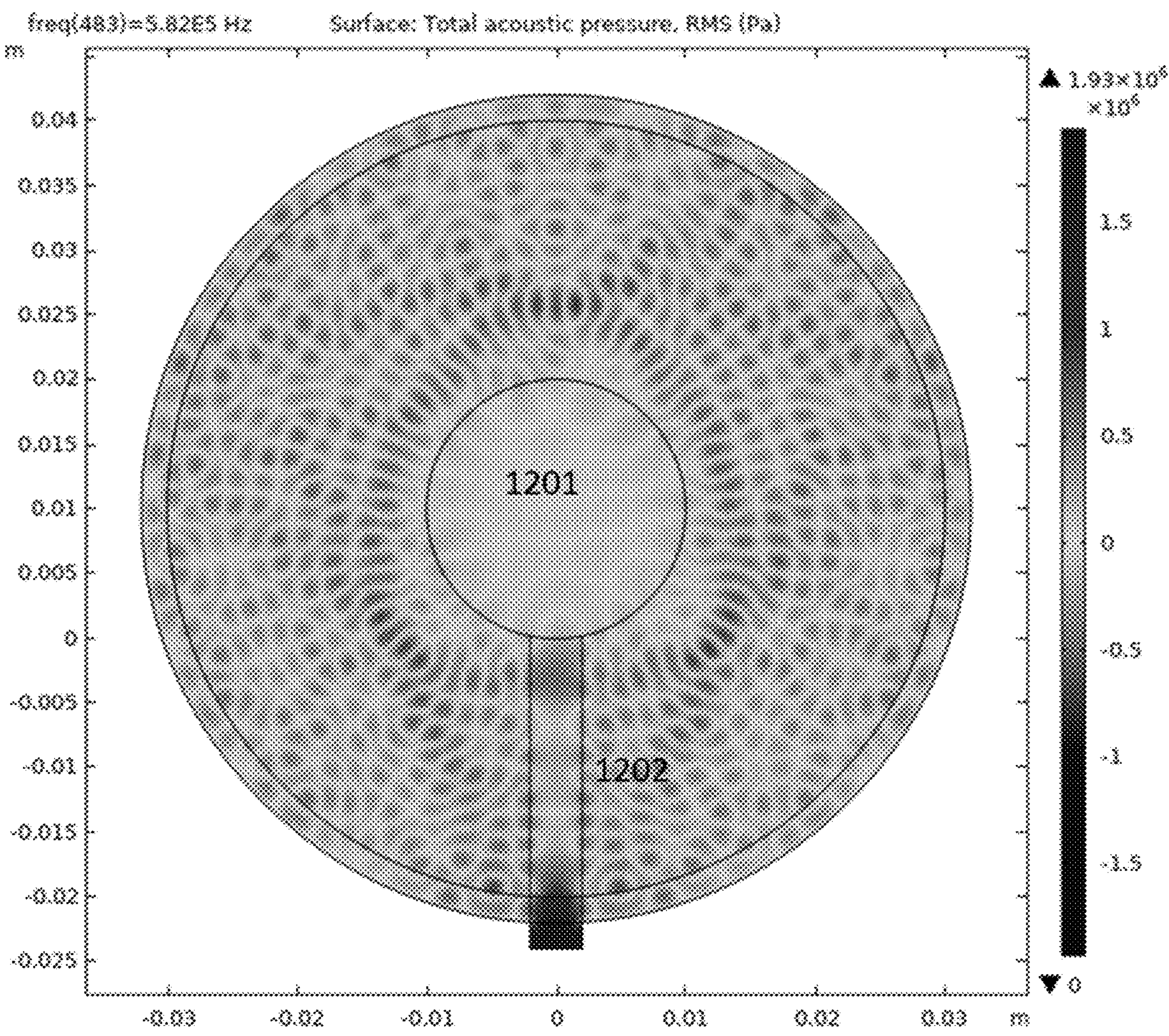

Another embodiment described herein deploys a comparatively rigid internal biocompatible probe to directly expose infected tissue to high cycle pressure swings while maintaining an acoustic pressure below the cavitation limit. FIG. 11A-E show the acoustic pressure profiles for the case of a steel pin (1101) in direct mechanical contact with the inner bone (1102) and an excitation amplitude of 8 nm. Sharp resonances that selectively deposit energy into the infected bone are evident in the figure, as seen for the pressure distributions at 314, 316, and 320 kHz, though this approach may obviously be adapted to generating high cycle fatigue in the tissue surrounding the bone by using the bone surface as a secondary transducer because it is substantially stiffer than the muscle or skin in this simplified example. Referring to FIG. 12A, 592 kHz excitation (1201) enhances treatment where the skin-muscle interface is preferentially treated while (FIG. 12B) at 582 kHz (1202) most of the acoustic energy is distributed within the muscle tissue.

Another embodiment described herein exposes fluid circulating ex vivo as in an extracorporeal membrane oxygenation (ECMO) system used in critical care, or a Heart-Lung Machine used in cardiac surgery. A section of the tubing through which blood is pumped is exposed to cyclic fatigue by acoustic radiation. The shape of the transducer surrounding the tubing is optimized to account for acoustic propagation into the fluid through the tubing wall with excitation frequency and amplitude adjusted to keep the peak pressure below the cavitation threshold of the circulating blood, as described for the in vitro cuvette shown in FIG. 2. The length of tubing exposed to acoustic radiation is determined by the need to ensure an adequate number of pressure cycles based on the applied frequency and the fluid's velocity through the tubing. These adaptations are obvious to those practiced in the art of acoustic propagation and fluid dynamics based on the foregoing disclosures.

Figure 13:
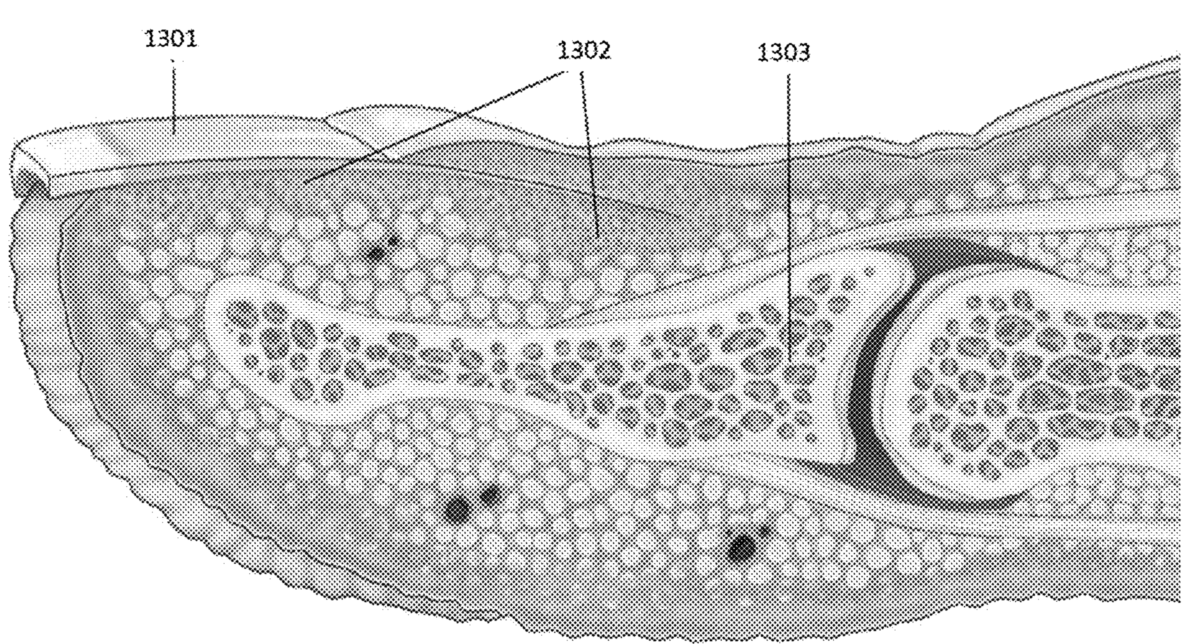
FIG. 13 shows a schematic anatomy of a human toe illustrating the relationships among the nail, nail bed, bone, and soft tissues.

Another embodiment of the method for treatment of toenail fungus is understood with reference to FIG. 13. Fungi (molds) such as *Candida albicans* are known to infect the nail beds (1302) of human toes and fingers. The anatomy of a human toe sketched in FIG. 13 shows the geometric relationships of the relatively stiff bone (1303) and nail (1301) in relation to the soft tissues including the nail bed (1302). A finite element model of the toe can be constructed using measured mechanical properties of each tissue and a tomographic image of the subject's toe. An acoustic transducer is placed in intimate contact, preferably with an adhesive cement such as cyanoacrylate, at a location on the toenail that provides high cycle disruption of the fungal sheath without inducing cavitation in the surrounding tissue. Excitation of the nail produces sound waves that propagate from the inner surface of the nail with scattering by the bone and skin-air interfaces as required by the laws of acoustics. Preferably one evaluates an anthropometric range of physiological geometries and mechanical properties of phalanges and determines by iterative calculation a range of acoustic frequencies, amplitudes, durations, and transducer geometries to accommodate most patients without the need for tomographic imaging.

Figure 14:
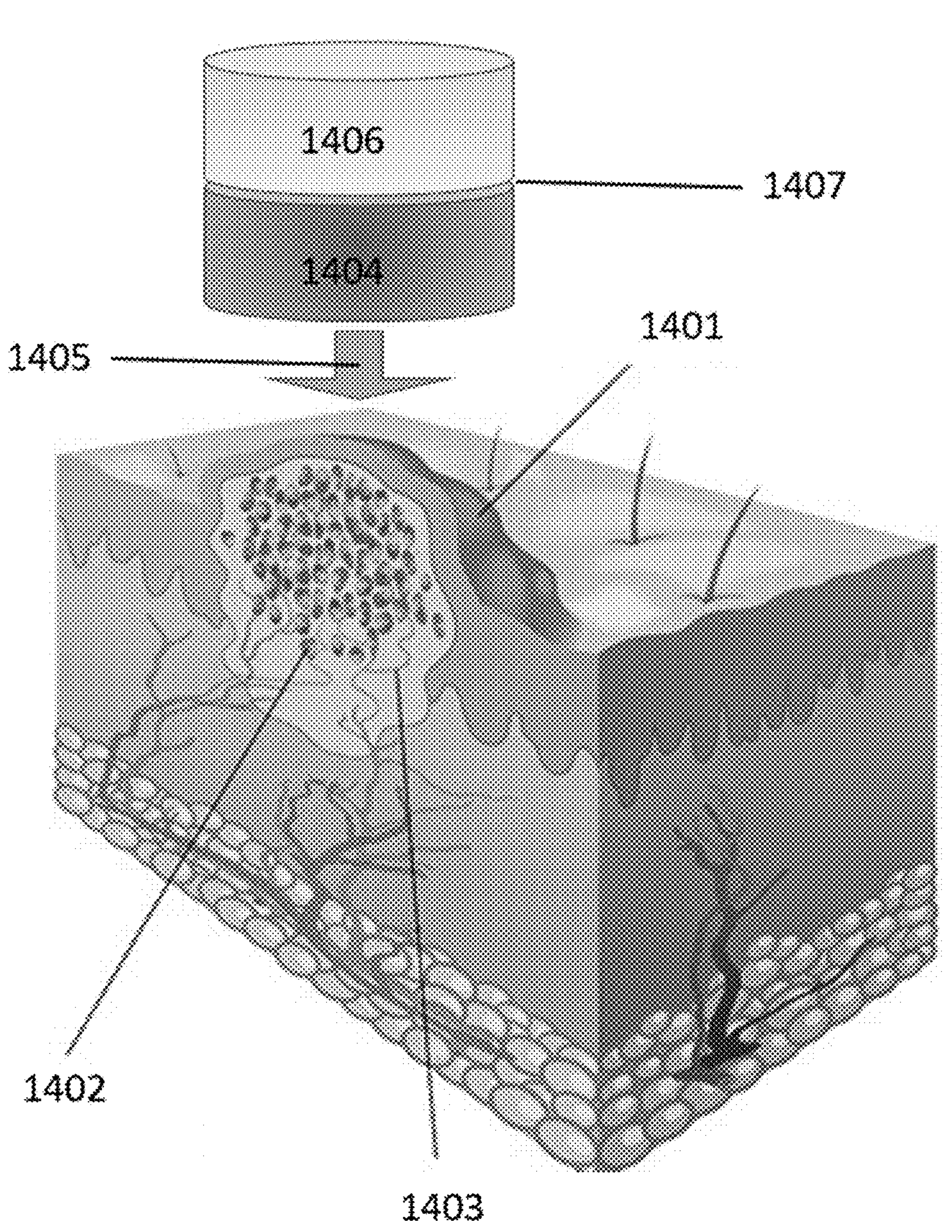
FIG. 14 shows a schematic rendering of a wart showing the virus infected cells (1402) with an external transducer (1404) that makes intimate mechanical contact (1403) with the epidermal surface.

Another embodiment may be understood by referring to the schematic rendering of a plantar wart in FIG. 14. Human papilloma virus infects epidermal cells (1402) that form a coherent cluster underneath the epidermis (1401) that is supplied with blood through vessels (1403). A rigid probe tip (1404) is separated from the body of the probe (1406) by a piezoelectric element (1407). The probe makes intimate mechanical contact (1405) with the epidermal surface and establishes an acoustic boundary condition in the vicinity of the wart. Finite element estimates of the acoustic pressure field are used to account for the varied impedances of solid and liquid structural features of the tissue as described above to adjust the amplitude, frequency, and duration of stimulation to fatigue the viral capsids without disrupting healthy cells.

Another exemplary embodiment describes a method and device to determine and apply acoustic energy to teeth for the impairment of adsorbed bacteria or fungi and will be obvious to those practiced in the arts of acoustic propagation and high cycle fatigue.

One embodiment described herein is a method for selectively diminishing viability of or killing a pathogen in a surrounding medium containing somatic cells by administering greater than ten thousand cycles of pressure variation below the threshold for cavitation of the surrounding medium. In one aspect, the pathogen is a cell having an internal static pressure of greater than 20 kPa above that of the surrounding medium. In another aspect, the pathogen is a bacterium. In another aspect, the pathogen is a fungus. In another aspect, the pathogen is a virus. In another aspect, the administration is by an acoustic transducer where the shape, frequency, amplitude, and orientation of the acoustic transducer is selected by finite element acoustic analysis of the surrounding medium and of the pathogen. In another aspect, the acoustic analysis permits application of pressure cycles at specific sites without causing excessive frictional heating or cavitation. In another aspect, the acoustic transducer is external to a human body of a subject. In another aspect, the acoustic transducer penetrates the human body of the subject to make acoustic contact with a targeted tissue or an internal structure. In another aspect, the acoustic transducer is shaped and excited to irradiate an extracorporeal fluid with greater than ten thousand cycles of pressure variation, wherein the amplitude, frequency, and number of the cycles of pressure variation diminish pathogen viability without causing cavitation or excessive heating of the surrounding medium. In another aspect, the cycles of pressure variation are selected to enable, accelerate, or potentiate the action of an antimicrobial pharmaceutical agent. In another aspect, the surrounding medium geometry and composition are determined by biomedical imaging. In another aspect, the biomedical imaging is tomographic. In another aspect, the acoustic transducer is a conformable piezoelectric transducer array, comprising: a silicone elastomer substrate and a silicone elastomer superstrate; a plurality of piezoelectric transducer elements disposed between the substrates and superstrate; a first electrical interconnect layer electrically interconnecting a first surface of the plurality of piezoelectric transducer elements adjacent to the silicone elastomer substrate; and a second electrical interconnect layer electrically interconnecting a second surface of the plurality of piezoelectric transducer elements adjacent to the silicone elastomer superstrate. In another aspect, at least one of the plurality of piezoelectric transducer elements comprises a 1-3 composite material. In another aspect, each of the plurality of piezoelectric transducer elements comprises a 1-3 composite material. In another aspect, the first and second electrical interconnect layers have a patterned island and bridge structure that includes a plurality of islands electrically interconnected by bridges, each of the plurality of piezoelectric transducer elements being supported by one of the islands.

Another embodiment described herein is a method for treating a subject infected by one or more pathogens using an acoustic transducer to selectively diminish the viability of or kill the one or more pathogens, the method comprising: contacting the acoustic transducer to an external surface of the subject's body such that the acoustic transducer conforms to a shape of the external surface, the acoustic transducer being a conformable piezoelectric transducer array, comprising: a silicone elastomer substrate and a silicone elastomer superstrate; a plurality of piezoelectric transducer elements disposed between the substrates and superstrate; a first electrical interconnect layer electrically interconnecting a first surface of the plurality of piezoelectric transducer elements adjacent to the silicone elastomer substrate; and a second electrical interconnect layer electrically interconnecting a second surface of the plurality of piezoelectric transducer elements adjacent to the silicone elastomer superstrate; and administering greater than ten thousand cycles of pressure variation into the subject using the acoustic transducer to penetrate the surface of the subject's body and make acoustic contact with the one or more pathogens. In one aspect, the method further comprises, optionally imaging the subject's body prior to and/or following the administering greater than ten thousand cycles of pressure variation, where the imaging comprises: transmitting ultrasound waves into the subject's body using the piezoelectric transducer array; receiving ultrasound waves from the subject body using the piezoelectric transducer array; and displaying an indication of the received ultrasound waves. In another aspect, the one or more pathogens is a cell having an internal static pressure of greater than 20 kPa above that of a surrounding medium. In another aspect, the one or more pathogens is a bacterium, fungus, virus, or combinations thereof. In another aspect, the cycles of pressure variation are below the threshold for cavitation or excessive heating of the surrounding medium. In another aspect, at least one of the plurality of piezoelectric transducer elements comprises a 1-3 composite material. In another aspect, each of the plurality of piezoelectric transducer elements comprises a 1-3 composite material. In another aspect, the first and second electrical interconnect layers have a patterned island and bridge structure that includes a plurality of islands electrically interconnected by bridges, each of the plurality of piezoelectric transducer elements being supported by one of the islands.

Another embodiment described herein is an acoustic transducer in mechanical contact with a living organism, the acoustic transducer configured to generate high cycle acoustic pressures for selectively diminishing the viability of or killing a pathogen without disrupting the living organism's somatic cells. In one aspect, the acoustic transducer is affixed to a surface of the living organism with an adhesive cement. In another aspect, the acoustic transducer penetrates a tissue of the living organism and makes acoustic contact with an internal structure whose elastic modulus exceeds that of a surrounding tissue. In another aspect, the internal structure is a bone. In another aspect, the internal structure is an implanted inorganic material. In another aspect, the internal structure is a metallic, ceramic, biomimetic composite, or biocompatible material. In another aspect, the acoustic transducer contacts a surface of a wart or lesion on the living organism generated by a viral, bacterial, or fungal infection. In another aspect, the acoustic transducer directs transient external pressures to an abscess on the living organism. In another aspect, the acoustic transducer directs transient external pressures to one or more teeth of the living organism for diminishing the viability or killing of adsorbed bacteria or fungi. In another aspect, the high cycle acoustic pressures comprise greater than ten thousand cycles of pressure variation. In another aspect, the acoustic transducer is a conformable piezoelectric transducer array, comprising: a silicone elastomer substrate and a silicone elastomer superstrate; a plurality of piezoelectric transducer elements disposed between the substrates and superstrate; a first electrical interconnect layer electrically interconnecting a first surface of the plurality of piezoelectric transducer elements adjacent to the silicone elastomer substrate; and a second electrical interconnect layer electrically interconnecting a second surface of the plurality of piezoelectric transducer elements adjacent to the silicone elastomer superstrate. In another aspect, at least one of the plurality of piezoelectric transducer elements comprises a 1-3 composite material. In another aspect, each of the plurality of piezoelectric transducer elements comprises a 1-3 composite material. In another aspect, the first and second electrical interconnect layers have a patterned island and bridge structure that includes a plurality of islands electrically interconnected by bridges, each of the plurality of piezoelectric transducer elements being supported by one of the islands.

Another embodiment described herein is the use of any of the methods described herein or the transducers described herein for selectively diminishing viability of or killing a pathogen in a surrounding medium containing somatic cells by administering greater than ten thousand cycles of pressure variation below the threshold for cavitation of the surrounding medium in a subject in need thereof.

It will be apparent to one of ordinary skill in the relevant art that suitable modifications and adaptations to the compositions, formulations, methods, processes, and applications described herein can be made without departing from the scope of any embodiments or aspects thereof. The compositions and methods provided are exemplary and are not intended to limit the scope of any of the specified embodiments. All of the various embodiments, aspects, and options disclosed herein can be combined in any variations or iterations. The scope of the compositions, formulations, methods, and processes described herein include all actual or potential combinations of embodiments, aspects, options, examples, and preferences herein described. The exemplary compositions and formulations described herein may omit any component, substitute any component disclosed herein, or include any component disclosed elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms or phrases in this disclosure are controlling. Furthermore, the foregoing discussion discloses and describes merely exemplary embodiments. All patents and publications cited herein are incorporated by reference herein for the specific teachings thereof.

Various embodiments and aspects of the inventions described herein are summarized by the following clauses:

Clause 1. A method for selectively diminishing viability of or killing a pathogen in a surrounding medium containing somatic cells by administering greater than ten thousand cycles of pressure variation below the threshold for cavitation of the surrounding medium.

Clause 2. The method of clause 1, wherein the pathogen is a cell having an internal static pressure of greater than 20 kPa above that of the surrounding medium.

Clause 3. The method of clause 1 or 2, wherein the pathogen is a bacterium.

Clause 4. The method of any one of clauses 1-3, wherein the pathogen is a fungus.

Clause 5. The method of any one of clauses 1-4, wherein the pathogen is a virus.

Clause 6. The method of any one of clauses 1-5, wherein the administration is by an acoustic transducer where the shape, frequency, amplitude, and orientation of the acoustic transducer is selected by finite element acoustic analysis of the surrounding medium and of the pathogen.

Clause 7. The method of any one of clauses 1-6, wherein the acoustic analysis permits application of pressure cycles at specific sites without causing excessive frictional heating or cavitation.

Clause 8. The method of any one of clauses 1-7, wherein the acoustic transducer is external to a human body of a subject.

Clause 9. The method of any one of clauses 1-8, wherein the acoustic transducer penetrates the human body of the subject to make acoustic contact with a targeted tissue or an internal structure.

Clause 10. The method of any one of clauses 1-9, wherein the acoustic transducer is shaped and excited to irradiate an extracorporeal fluid with greater than ten thousand cycles of pressure variation, wherein the amplitude, frequency, and number of the cycles of pressure variation diminish pathogen viability without causing cavitation or excessive heating of the surrounding medium.

Clause 11. The method of any one of clauses 1-10, wherein the cycles of pressure variation are selected to enable, accelerate, or potentiate the action of an antimicrobial pharmaceutical agent.

Clause 12. The method of any one of clauses 1-11, wherein the surrounding medium geometry and composition are determined by biomedical imaging.

Clause 13. The method of any one of clauses 1-12, wherein the biomedical imaging is tomographic.

Clause 14. The method of any one of clauses 1-13, wherein the acoustic transducer is a conformable piezoelectric transducer array, comprising:

a silicone elastomer substrate and a silicone elastomer superstrate;

a plurality of piezoelectric transducer elements disposed between the substrates and superstrate;

a first electrical interconnect layer electrically interconnecting a first surface of the plurality of piezoelectric transducer elements adjacent to the silicone elastomer substrate; and a second electrical interconnect layer electrically interconnecting a second surface of the plurality of piezoelectric transducer elements adjacent to the silicone elastomer superstrate.

Clause 15. The method of any one of clauses 1-14, wherein at least one of the plurality of piezoelectric transducer elements comprises a 1-3 composite material.

Clause 16. The method of any one of clauses 1-15, wherein each of the plurality of piezoelectric transducer elements comprises a 1-3 composite material.

Clause 17. The method of any one of clauses 1-16, wherein the first and second electrical interconnect layers have a patterned island and bridge structure that includes a plurality of islands electrically interconnected by bridges, each of the plurality of piezoelectric transducer elements being supported by one of the islands.

Clause 18. A method for treating a subject infected by one or more pathogens using an acoustic transducer to selectively diminish the viability of or kill the one or more pathogens, the method comprising:

contacting the acoustic transducer to an external surface of the subject's body such that the acoustic transducer conforms to a shape of the external surface, the acoustic transducer being a conformable piezoelectric transducer array, comprising:

a silicone elastomer substrate and a silicone elastomer superstrate;

a plurality of piezoelectric transducer elements disposed between the substrates and superstrate;

a first electrical interconnect layer electrically interconnecting a first surface of the plurality of piezoelectric transducer elements adjacent to the silicone elastomer substrate; and a second electrical interconnect layer electrically interconnecting a second surface of the plurality of piezoelectric transducer elements adjacent to the silicone elastomer superstrate; and administering greater than ten thousand cycles of pressure variation into the subject using the acoustic transducer to penetrate the surface of the subject's body and make acoustic contact with the one or more pathogens.

Clause 19. The method of clause 18 further comprising, optionally imaging the subject's body prior to and/or following the administering greater than ten thousand cycles of pressure variation, where the imaging comprises:

transmitting ultrasound waves into the subject's body using the piezoelectric transducer array;

receiving ultrasound waves from the subject body using the piezoelectric transducer array; and displaying an indication of the received ultrasound waves.

Clause 20. The method of clause 18 or 19, wherein the one or more pathogens is a cell having an internal static pressure of greater than 20 kPa above that of a surrounding medium.

Clause 21. The method of any one of clauses 18-20, wherein the one or more pathogens is a bacterium, fungus, virus, or combinations thereof.

Clause 22. The method of any one of clauses 18-21, wherein the cycles of pressure variation are below the threshold for cavitation or excessive heating of the surrounding medium.

Clause 23. The method of any one of clauses 18-22, wherein at least one of the plurality of piezoelectric transducer elements comprises a 1-3 composite material.

Clause 24. The method of any one of clauses 18-23, wherein each of the plurality of piezoelectric transducer elements comprises a 1-3 composite material.

Clause 25. The method of any one of clauses 18-24, wherein the first and second electrical interconnect layers have a patterned island and bridge structure that includes a plurality of islands electrically interconnected by bridges, each of the plurality of piezoelectric transducer elements being supported by one of the islands.

Clause 26. An acoustic transducer in mechanical contact with a living organism, the acoustic transducer configured to generate high cycle acoustic pressures for selectively diminishing the viability of or killing a pathogen without disrupting the living organism's somatic cells.

Clause 27. The acoustic transducer of clause 26, wherein the acoustic transducer is affixed to a surface of the living organism with an adhesive cement.

Clause 28. The acoustic transducer of clause 26 or 27, wherein the acoustic transducer penetrates a tissue of the living organism and makes acoustic contact with an internal structure whose elastic modulus exceeds that of a surrounding tissue.

Clause 29. The acoustic transducer of any one of clauses 26-28, wherein the internal structure is a bone.

Clause 30. The acoustic transducer of any one of clauses 26-29, wherein the internal structure is an implanted inorganic material.

Clause 31. The acoustic transducer of any one of clauses 26-30, wherein the internal structure is a metallic, ceramic, biomimetic composite, or biocompatible material.

Clause 32. The acoustic transducer of any one of clauses 26-31, wherein the acoustic transducer contacts a surface of a wart or lesion on the living organism generated by a viral, bacterial, or fungal infection.

Clause 33. The acoustic transducer of any one of clauses 26-32, wherein the acoustic transducer directs transient external pressures to an abscess on the living organism.

Clause 34. The acoustic transducer of any one of clauses 26-33, wherein the acoustic transducer directs transient external pressures to one or more teeth of the living organism for diminishing the viability or killing of adsorbed bacteria or fungi.

Clause 35. The acoustic transducer of any one of clauses 26-34, wherein the high cycle acoustic pressures comprise greater than ten thousand cycles of pressure variation.

Clause 36. The acoustic transducer of any one of clauses 26-35, wherein the acoustic transducer is a conformable piezoelectric transducer array, comprising:

- a silicone elastomer substrate and a silicone elastomer superstrate;
- a plurality of piezoelectric transducer elements disposed between the substrates and superstrate;
- a first electrical interconnect layer electrically interconnecting a first surface of the plurality of piezoelectric transducer elements adjacent to the silicone elastomer substrate; and
- a second electrical interconnect layer electrically interconnecting a second surface of the plurality of piezoelectric transducer elements adjacent to the silicone elastomer superstrate.

Clause 37. The acoustic transducer of any one of clauses 26-36, wherein at least one of the plurality of piezoelectric transducer elements comprises a 1-3 composite material.

Clause 38. The acoustic transducer of any one of clauses 26-37, wherein each of the plurality of piezoelectric transducer elements comprises a 1-3 composite material.

Clause 39. The acoustic transducer of any one of clauses 26-38, wherein the first and second electrical interconnect layers have a patterned island and bridge structure that includes a plurality of islands electrically interconnected by bridges, each of the plurality of piezoelectric transducer elements being supported by one of the islands.

Clause 40. Use of the method of any one of clauses 1-17 or 18-39, or the transducer of any one of clauses 26-39, for selectively diminishing viability of or killing a pathogen in a surrounding medium containing somatic cells by administering greater than ten thousand cycles of pressure variation below the threshold for cavitation of the surrounding medium in a subject in need thereof.

What is claimed:

1. A method for selectively killing or diminishing viability of a pathogen infecting a mammalian subject tissue, the method comprising:

- contacting a mammalian subject tissue with one or more acoustic transducers; and
- administering greater than ten thousand cycles of pressure variation below a threshold for cavitation of the mammalian subject tissue, whereby the greater than ten thousand cycles of pressure variation is sufficient to kill or diminish viability of a pathogen infecting the mammalian subject tissue without harming the mammalian subject tissue;
- with the proviso that the only form of energy administered to kill or diminish the viability of the pathogen is acoustic energy.

2. The method of claim 1, wherein the pathogen is a cell having an internal static pressure of greater than 20 kPa above that of the mammalian subject tissue.

3. The method of claim 1, wherein the pathogen is a bacterium.

4. The method of claim 1, wherein the pathogen is a fungus.

5. The method of claim 1, wherein the pathogen is a virus.

6. The method of claim 1, wherein the shape, frequency, amplitude, and orientation of the one or more acoustic transducers is selected by finite element acoustic analysis of the mammalian subject tissue and of the pathogen.

7. The method of claim 6, wherein the finite element acoustic analysis permits application of pressure cycles at specific mammalian subject tissue sites without causing excessive heating.

8. The method of claim 1, wherein the one or more acoustic transducers are external to the mammalian subject tissue.

9. The method of claim 1, wherein the one or more acoustic transducers penetrate the mammalian subject tissue to make acoustic contact with a targeted tissue or an internal structure.

10. The method of claim 1, wherein the one or more acoustic transducers are shaped and excited to irradiate an extracorporeal fluid with greater than ten thousand cycles of pressure variation, wherein the amplitude, frequency, and number of the greater than ten thousand cycles of pressure variation diminish pathogen viability without causing excessive heating of the mammalian subject tissue.

11. The method of claim 1, wherein the greater than ten thousand cycles of pressure variation are selected to enable, accelerate, or potentiate the action of an antimicrobial pharmaceutical agent.

12. The method of claim 1, wherein the mammalian subject tissue geometry and composition are determined by biomedical imaging.

13. The method of claim 12, wherein the biomedical imaging is tomographic.

14. The method of claim 1, wherein the one or more acoustic transducers are arranged in a conformable piezoelectric transducer array, comprising:

a silicone elastomer substrate and a silicone elastomer superstrate;

a plurality of piezoelectric transducer elements disposed between the silicone elastomer substrate and the silicone elastomer superstrate;

a first electrical interconnect layer electrically interconnecting a first surface of the plurality of piezoelectric transducer elements adjacent to the silicone elastomer substrate; and a second electrical interconnect layer electrically interconnecting a second surface of the plurality of piezoelectric transducer elements adjacent to the silicone elastomer superstrate.

15. The method of claim 14, wherein at least one of the plurality of piezoelectric transducer elements comprises a composite material.

16. The method of claim 14, wherein each of the plurality of piezoelectric transducer elements comprises a composite material.

17. The method of claim 14, wherein the first and second electrical interconnect layers have a patterned island and bridge structure that includes a plurality of islands electrically interconnected by bridges, each of the plurality of piezoelectric transducer elements being supported by one of the plurality of islands.

18. A method for treating a mammalian subject infected by one or more pathogens using an acoustic transducer to selectively kill or diminish viability of the one or more pathogens, the method comprising:

contacting the acoustic transducer to an external surface of the mammalian subject such that the acoustic transducer conforms to the external surface, the acoustic transducer being a conformable piezoelectric transducer array, comprising:

a silicone elastomer substrate and a silicone elastomer superstrate;

a plurality of piezoelectric transducer elements disposed between the silicone elastomer substrate and silicone elastomer superstrate;

a first electrical interconnect layer electrically interconnecting a first surface of the plurality of piezoelectric transducer elements adjacent to the silicone elastomer substrate; and a second electrical interconnect layer electrically interconnecting a second surface of the plurality of piezoelectric transducer elements adjacent to the silicone elastomer superstrate; and administering greater than ten thousand cycles of pressure variation below a threshold for cavitation of the mammalian subject, whereby the greater than ten thousand cycles of pressure variation is sufficient to kill or diminish viability of the one or more pathogens infecting the mammalian subject without harming the mammalian subject;

with the proviso that the only form of energy administered to kill or diminish the viability of the one or more pathogens is acoustic energy.

19. The method of claim 18, further comprising, imaging the mammalian subject prior to and following the administering greater than ten thousand cycles of pressure variation, where the imaging comprises:

transmitting ultrasound waves into the mammalian subject using the confromable piezoelectric transducer array;

receiving ultrasound waves from the mammalian subject using the conformable piezoelectric transducer array; and displaying an indication of the received ultrasound waves.

20. The method of claim 18, wherein the one or more pathogens is a cell having an internal static pressure of greater than 20 kPa above that of the mammalian subject.

21. The method of claim 18, wherein the one or more pathogens is a bacterium, fungus, virus, or combinations thereof.

22. The method of claim 18, wherein the greater than ten thousand cycles of pressure variation are below a threshold for excessive heating of a tissue of the mammalian subject.

23. The method of claim 18, wherein at least one of the plurality of piezoelectric transducer elements comprises a composite material.

24. The method of claim 18, wherein each of the plurality of piezoelectric transducer elements comprises a composite material.

25. The method of claim 18, wherein the first and second electrical interconnect layers have a patterned island and bridge structure that includes a plurality of islands electrically interconnected by bridges, each of the plurality of piezoelectric transducer elements being supported by one of the islands.

* * * * *